US009822301B2

(12) United States Patent
Tojo et al.

(10) Patent No.: US 9,822,301 B2
(45) Date of Patent: Nov. 21, 2017

(54) ALKENYL ETHER COMPOUND AND A LIQUID CRYSTAL COMPOSITION USING THE SAME

(71) Applicant: DIC Corporation, Tokyo (JP)

(72) Inventors: Kenta Tojo, Kita-adachi-gun (JP); Takashi Matsumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/104,428

(22) PCT Filed: Nov. 13, 2014

(86) PCT No.: PCT/JP2014/080044
§ 371 (c)(1),
(2) Date: Jun. 14, 2016

(87) PCT Pub. No.: WO2015/093193
PCT Pub. Date: Jun. 25, 2015

(65) Prior Publication Data
US 2016/0326433 A1    Nov. 10, 2016

(30) Foreign Application Priority Data
Dec. 16, 2013  (JP) .................................. 2013-259103

(51) Int. Cl.
*C07C 41/00* (2006.01)
*C09K 19/30* (2006.01)
*C07C 43/225* (2006.01)
*C09K 19/04* (2006.01)
*G02F 1/1333* (2006.01)
*G02F 1/1339* (2006.01)
*G02F 1/1341* (2006.01)
*C09K 19/12* (2006.01)

(52) U.S. Cl.
CPC ........ *C09K 19/3003* (2013.01); *C07C 43/225* (2013.01); *C09K 19/0403* (2013.01); *G02F 1/1339* (2013.01); *G02F 1/1341* (2013.01); *G02F 1/13394* (2013.01); *G02F 1/133377* (2013.01); *C07C 2601/14* (2017.05); *C09K 2019/0444* (2013.01); *C09K 2019/121* (2013.01); *C09K 2019/123* (2013.01); *C09K 2019/301* (2013.01); *C09K 2019/3016* (2013.01); *C09K 2019/3019* (2013.01); *G02F 2001/13398* (2013.01); *G02F 2001/13415* (2013.01)

(58) Field of Classification Search
None
See application file for complete search history.

(56) References Cited

U.S. PATENT DOCUMENTS

| 4,551,264 A | 11/1985 | Eidenschink et al. |
| 4,990,305 A | 2/1991 | Foster et al. |
| 7,074,836 B1 * | 7/2006 | Kawada .................. C07C 15/14 514/650 |
| 2005/0161637 A1 | 7/2005 | Shinano et al. |
| 2008/0149890 A1 | 6/2008 | Irisawa et al. |
| 2008/0199635 A1 | 8/2008 | Hirschmann et al. |
| 2010/0320420 A1 | 12/2010 | Hirschmann et al. |
| 2011/0001090 A1 | 1/2011 | Wittek et al. |
| 2014/0034876 A1 | 2/2014 | Gotoh et al. |
| 2014/0084210 A1 | 3/2014 | Yanai et al. |
| 2014/0203209 A1 | 7/2014 | Gotoh et al. |
| 2016/0326433 A1 * | 11/2016 | Tojo .................. G02F 1/133377 |

FOREIGN PATENT DOCUMENTS

| CN | 102643653 A | 8/2012 |
| CN | 103013535 A | 4/2013 |
| CN | 103146392 A | 6/2013 |
| CN | 103194243 A | 7/2013 |
| CN | 103205264 A | 7/2013 |
| CN | 103242861 A | 8/2013 |
| CN | 103642502 A | 3/2014 |
| CN | 103642503 A | 3/2014 |
| CN | 103756688 A | 4/2014 |
| CN | 103772335 A | 5/2014 |
| CN | 103773386 A | 5/2014 |
| CN | 103773390 A | 5/2014 |
| CN | 103805211 A | 5/2014 |
| CN | 104087313 A | 10/2014 |
| DE | 199 59 721 A1 | 6/2000 |

(Continued)

OTHER PUBLICATIONS

International Search Report dated Feb. 10, 2015, issued in counterpart International Application No. PCT/JP2014/080044 (5 pages).

*Primary Examiner* — Clinton A Brooks
*Assistant Examiner* — Ana Z Muresan
(74) *Attorney, Agent, or Firm* — Westerman, Hattori, Daniels & Adrian, LLP

(57) ABSTRACT

The present invention provides a compound represented by general formula (1) as well as a liquid crystal composition containing this compound and a liquid crystal display using this liquid crystal composition. Using the compound represented by general formula (1) as a component of a liquid crystal composition makes it possible to obtain a liquid crystal composition having a low viscosity ($\eta$), a high $\Delta n$, suitable $T_{-i}$, high miscibility with other liquid crystal compounds, and presenting a liquid crystal phase over a wide temperature range. This is therefore extremely useful as a structural component of a liquid crystal composition for a liquid crystal display requiring a high speed response.

6 Claims, 1 Drawing Sheet

(56) References Cited

FOREIGN PATENT DOCUMENTS

| GB | 2 249 309 A | 5/1992 |
|---|---|---|
| JP | 61-291536 A | 12/1986 |
| JP | 6-293690 A | 10/1994 |
| JP | 7-82561 A | 3/1995 |
| JP | 7-258141 A | 10/1995 |
| JP | 2005-154724 A | 6/2005 |
| JP | 2005-154725 A | 6/2005 |
| JP | 2007-146023 A | 6/2007 |
| JP | 2007-277127 A | 10/2007 |
| JP | 2008-189927 A | 8/2008 |
| JP | 2011-506707 A | 3/2011 |
| JP | 2011-516628 A | 5/2011 |
| JP | 2014-40413 A | 3/2014 |
| JP | 2014-62212 A | 4/2014 |
| JP | 2014-156460 A | 8/2014 |
| WO | 2004/058676 A1 | 7/2004 |
| WO | 2006/061966 A1 | 6/2006 |
| WO | 2007/063681 A1 | 6/2007 |

* cited by examiner

[Fig. 1]
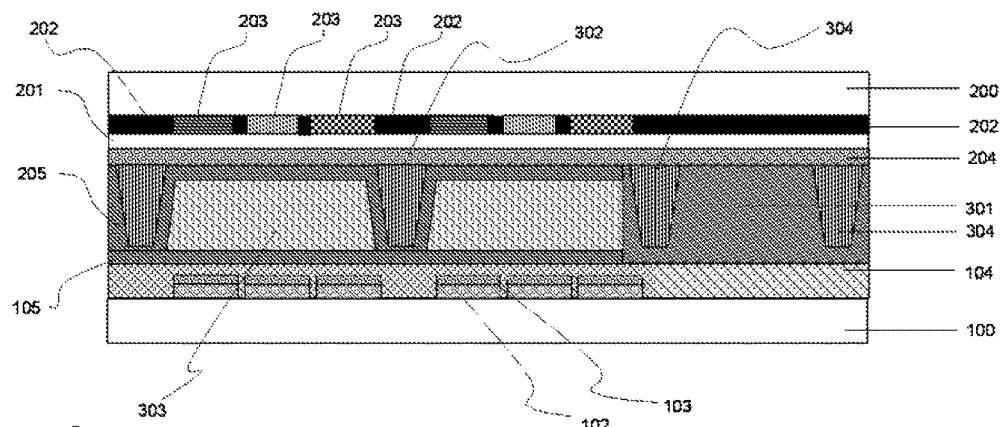
[Fig. 2]
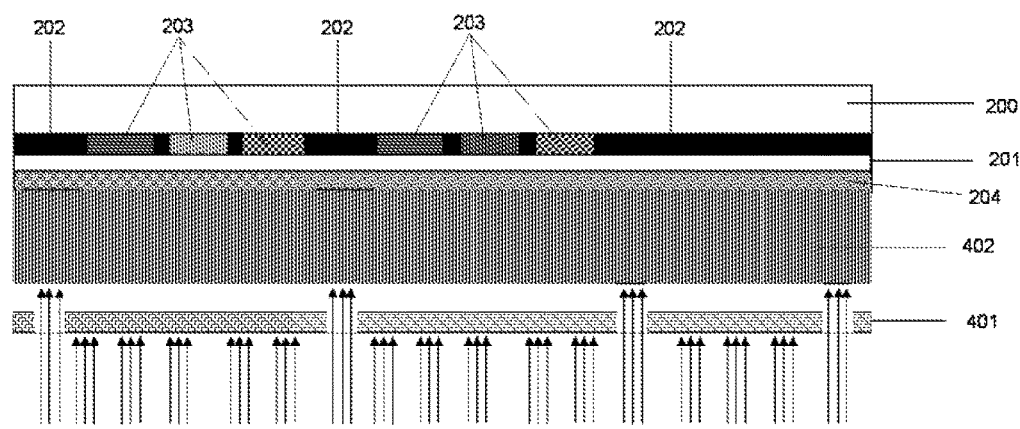

ALKENYL ETHER COMPOUND AND A LIQUID CRYSTAL COMPOSITION USING THE SAME

TECHNICAL FIELD

The present invention relates to a compound having an alkenyl ether structure useful as organic electronic materials, medicines and agricultural chemicals, and in particular, useful as the material for liquid crystal display devices.

BACKGROUND OF THE INVENTION

Liquid crystal display elements have been used in various devices such as measuring equipment, automotive panel word processor, electronic note, printer, computer, TV, clock, advertisement panel board, and etc., including watch and electronic calculator. The representative of the liquid crystal display method includes TN (twisted nematic) type, STN (super twisted nematic) type, vertical alignment type using a TFT (thin film transistor), and IPS (in-plane switching) type. Liquid crystal compositions used for such liquid crystal display devices need to satisfy the requirements as follows: they are stable to external elements such as moisture, air, heat, and light: having a liquid crystal phase (nematic phase, smectic phase, and blue phase, and etc.) in a broad temperature range as possible including room temperature as a center thereof; having a low viscosity; and enabling a low driving voltage. Furthermore, the liquid crystal composition comprises several to several tens of compounds in order to optimize the value of the dielectric constant anisotropy ($\Delta\epsilon$) and a refractive index anisotropy ($\Delta n$) depending on individual display element.

In all driving types such as such as TN type, STN type, and IPS type, there have been demands to improve the response speed, and in order to satisfy such demands, a liquid crystal composition having a lower viscosity than present liquid crystal compositions is required. In order to develop a liquid crystal composition having a low viscosity, it is known to be extremely effective to employ a non-polar compound, that is, a compound which show almost no $\Delta\epsilon$. For such a non-polar compound, it is demanded to have a suitable transparent point ($T_{-i}$), $\Delta n$, and a low viscosity. Also, a high stability to heat, light and etc., is required when it is uses as a liquid crystal composition for display element.

Conventionally, compounds having a cyclohexylvinyl structure or an allyl ether structure are used as a non-polar compound. A compound having an allyl ether structure is a useful compound that indicates a relatively low viscosity. For example, the compound shown below is disclosed as a compound having an allyl ether structure (Patent Reference No. 1). However, this compound is not large enough in its $\Delta n$ and has a problem of relatively low miscibility with other liquid crystalline compounds.

[Formula 1]

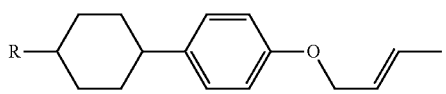

(In the formula, R represents a linear alkyl group with a carbon atom number of 1 to 9.)

On the other hand, for example, as a compound having a structure in which hydrogen atom of a benzene ring was substituted with fluorine atom, the compound shown below is disclosed (Patent Reference No. 2, Patent Reference No. 3).

[Formula 2]

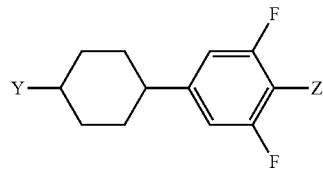

(In the formula, Y and Z each independently represent an alkyl group and an alkoxy group having a carbon atom number of 1 to 12.)

[Formula 3]

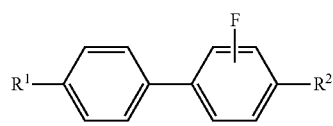

(In the formula, $R^1$ and $R^2$ each independently represent an alkyl group and an alkoxy group having a carbon atom number of 1 to 12.)

Furthermore, a compound having an allyl ether structure and a substituent of a halogen atom, as shown below, is disclosed (Patent Reference No. 4). However, the values of $\Delta n$ thereof are not large enough.

[Formula 4]

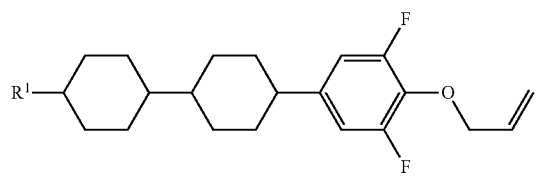

PRIOR ART REFERENCES

Patent References

Patent Reference No. 1: Japanese Laid-Open Patent Publication No. 61-291536;
Patent Reference No. 2: U.S. Pat. No. 4,551,264;
Patent Reference No. 3: U.S. Pat. No. 4,990,305; and
Patent Reference No. 4: Japanese Laid-Open Patent Publication No. 7-258141.

SUMMARY OF THE INVENTION

The Objectives to Solve by the Invention

The objects of the present invention are: to provide a compound having a low viscosity ($\eta$), a large $\Delta n$, and good miscibility with other liquid crystal compounds; to provide a liquid crystal composition containing such a compound; and to provide a liquid crystal display device containing it.

Means to Solve the Problem

In order to solve the objects above, the inventors of the present application have variously researched and found that the objects above can be effectively solved by a specific compound having a 2,6-difluoro-1-alkenyl ether structure, and accomplished the invention of the present application.

In the present invention, the general formula (1) is as follow.

[Formula 5]

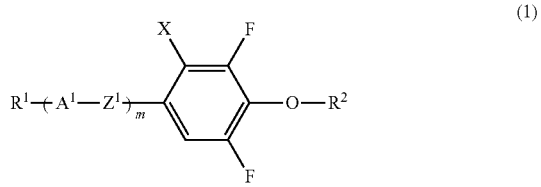

(1)

(In the formula, $R^1$ represents an alkyl group having a carbon atom number of 1 to 15 or an alkenyl group having a carbon atom number of 2 to 15, in which one group of —CH$_2$—, or two or more groups of —CH$_2$— not adjacent to each other can be replaced with a group of —O—, —S—, —COO—, —OCO— or —CO—, in which the hydrogen atom in these groups can be replaced with a fluorine atom; $R^2$ represents an alkenyl group having a carbon atom number of 2 to 5, in which among the —CH$_2$— groups existing in the alkenyl group, one —CH$_2$— group, or two or more —CH$_2$— groups not adjacent to each other, except for the —CH$_2$— group directly combined with an oxygen atom, can be replaced with —O—, —S—, —COO—, —OCO— or —CO—, in which the hydrogen atom existing in the alkenyl group can be replaced with a fluorine atom;
$A_1$ is selected from the groups consisting of:
(a): 1,4-cyclohexylene group (in which one —CH2- group or noncontiguous two or more —CH2- groups can be substituted with —O— or —S—);
(b): 1,4-phenylene group (in which in the group, one —CH═ group or noncontiguous two or more —CH═ groups can be replaced with —N═, and in which in the group, the hydrogen atom can be replaced with a fluorine atom.); and
(c): naphthalene-2,6-diyl group (in which in the group, one —CH═ group or noncontiguous two or more —CH═ groups can be replaced with —N═, and in which in the group, the hydrogen atom can be replaced with a fluorine atom.);
$Z^1$ represents —CH$_2$O—, —OCH$_2$—, —CF$_2$O—, —OCF$_2$—, —COO—, —OCO—, —CH$_2$CH$_2$—, —CF$_2$CF$_2$—, —CH═CH—, —CF═CF—, —C≡C— or a single bond;
X represents a hydrogen atom, a fluorine atom or a chlorine atom;
m represents 1 to 4, in which when m is 2 to 4, and plural $A^1$ groups exist, said plural $A^1$ group can be the same as or different from each other; and in which when m is 2 to 4, and plural $Z^1$ groups exist, said plural $Z^1$ groups can be the same as or different from each other.
However, when m represents 2 to 4, there is provided a compound in which at least one or more $A^1$ groups represent 1,4-phenylene group or naphthalene-2,6-diyl group.).
In this way, there is provided the compound represented by general formula (1) above, and also, there is provided a liquid crystal composition including the compound, and a liquid crystal display element using the liquid crystal composition.

Effects of the Invention

The novel liquid crystalline compound represented by general formula (1), as provided by the present invention, can be manufactured by an industrially easy processes, and thereby obtained compound represented by general formula (1) can exhibit a low viscosity and a large value of Δn, while maintaining a high level of chemical stability and a high level of miscibility with a liquid crystal composition.

Therefore, using the compound represented by general formula (1) as a component of a liquid crystal composition, it is possible to make the liquid crystal composition have a low viscosity. As a result, it can be very useful as a component of the liquid crystal composition for a liquid crystal display element which is demanded to be provided with a high speed response.

BRIEF DESCRIPTION OF THE DRAWINGS

FIG. 1 is a cross section view of the liquid crystal display element of the present invention. The substrate with elements 100 to 105 are referred to as "back plane," and the board with elements 200 to 205 are referred to as "front plane."

FIG. 2 illustrates processes of light exposure treatment using the pattern for producing the columnar spacers formed on the black matrix as a photo mask pattern.

EMBODIMENTS TO CARRY OUT THE INVENTION

In general formula (1), in order to reduce a viscosity, it is preferable that $R^1$ is an alkyl group having a carbon atom number of 1 to 8 or an alkenyl group having a carbon atom number of 2 to 8; and it is particularly preferable that it is an alkyl group having a carbon atom number of 1 to 5 or an alkenyl group having a carbon atom number of 2 to 5. Also, it is preferable that it is of a straight chain.

In order to reduce a viscosity, $R^2$ is preferably an alkenyl group having a carbon atom number of 2 to 6. In order to reduce a viscosity, $R^2$ is preferably an alkenyl group having a carbon atom number of 2 to 6.

[Formula 6]

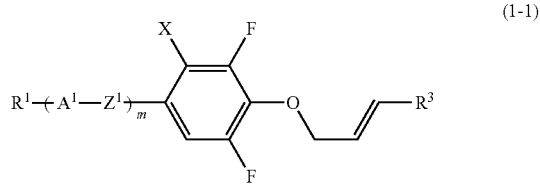

(1-1)

(In the formula, X, $R^1$, $A^1$, $Z^1$ and m each independently represent the same meaning as those of X, $R^1$, $A^1$, $Z^1$ and m of the general formula (1),
$R^3$ represents a hydrogen atom or an alkyl group having a carbon atom number of 1 to 3, in which one —CH$_2$— group, or two or more —CH$_2$— group not adjacent to each other can be replaced with a group of —O—, —S—, —COO—, —OCO— or —CO—, in which the hydrogen atom in these groups can be replaced with a fluorine atom.) Furthermore, in order to reduce a viscosity, $R^2$ is preferably an alkenyl group having a carbon atom number of 2 to 5.

[Formula 7]

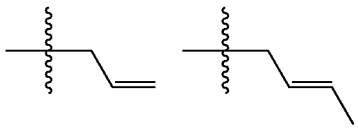

The above is preferable.

It is preferable that $A^1$ is each independently trans-1,4-cyclohexylene group, unsubstituted naphthalene-2,6-diyl group, or unsubstituted 1,4-phenylene group in order to reduce a viscosity. It is more preferable that it is trans-1,4-cyclohexylene group. To improve a miscibility with other liquid crystalline components, the following is preferable.

[Formula 8]

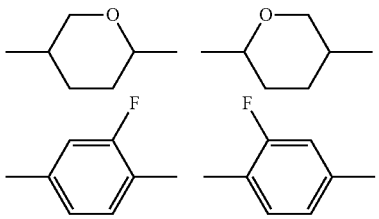

The above is preferable. Also, it is preferable that $A^1$ is each independently naphthalene-2,6-diyl group or 1,4-phenylene group to make large a value of $\Delta n$. It is preferable that the ratio of the 1,4-phenylene group and the naphthalene-2,6-diyl group occupied in all the ring structures in the compound is relatively high. It is preferable that the ratio is 40% or more; or more preferably 50% or more; or more further preferably 60% or more; and yet more preferably 100%. In detail, when m is 1, and when $A^1$ is trans-1,4-cyclohexylene group, naphthalene-2,6-diyl group or 1,4-phenylene group, this case is preferable since the ratio of the 1,4-phenylene group and the naphthalene-2,6-diyl group in all the ring structures in the compound becomes 50% or more. When m is 2 and when at least one or more of $A^1$ is or are 1,4-phenylene group or naphthalene-2,6-diyl group, this case is preferable since the ratio of the 1,4-phenylene group and the naphthalene-2,6-diyl group in all the ring structures in the compound becomes 50% or more. In addition, it is preferable that $A^1$ each independently represents 1,4-phenylene group or naphthalene-2,6-diyl group in order to increase the ratio above. When m is 3 and when at least one of $A^1$ is 1,4-phenylene group or naphthalene-2,6-diyl group, this case is preferable since the ratio of the 1,4-phenylene group and the naphthalene-2,6-diyl group in all the ring structures in the compound becomes 50% or more. In addition, it is preferable that at least two of $A^1$ represent 1,4-phenylene group or naphthalene-2,6-diyl group in order to increase the ratio above. When m is 4 and when at least one of $A^1$ is 1,4-phenylene group or naphthalene-2,6-diyl group, this case is preferable since the ratio of the 1,4-phenylene group and the naphthalene-2,6-diyl group in all the ring structures in the compound becomes 40% or more. In addition, it is preferable that at least two of $A^1$ represent 1,4-phenylene group or naphthalene-2,6-diyl group in order to increase the ratio above. It is preferable that the ratio is made as high as possible within the preferable range if the value of $\Delta n$ is given weight. By contrast, it is preferable that the ratio is made as low as possible within the preferable range if the viscosity and the miscibility with other liquid crystalline components are given weight.

In order to improve a long-term reliability when it is made into a liquid crystal display element, it is preferable that it does not include a nitrogen atom and a chlorine atom, and that the ring structure thereof does not include a cyclohexene-1,4-diyl group having an unsaturated bond.

It is preferable that X is a hydrogen atom when the viscosity is given weight, and it is preferable that it is a fluorine atom when the miscibility with other liquid crystalline components is given weight.

It is preferable that $Z^1$ is —CH$_2$O—, —OCH$_2$—, —CF$_2$O—, —OCF$_2$—, —CF=CF—, —C≡C— or a single bond in order to reduce a viscosity; it is more preferable that it is —CF$_2$O—, —OCF$_2$—, —CH$_2$CH$_2$— or a single bond; and specifically it is preferable that it is a single bond.

It is preferable that m is 1 or 2 when the viscosity is given weight, and it is preferable that it is 3 or 4 when $T_{ni}$ is given weight. It is preferably 2 or 3 in order to increase the miscibility with the liquid crystal composition.

In addition, in the compound represented by general formula (1), it does not become a structure in which heteroatoms are directly connected to each other.

Specific examples of preferable compounds are shown below, but the present invention is not limited thereto.

In general formula (1), the compounds represented by general formula (1a) to general formula (1d) shown below are each preferable.

[Formula 9]

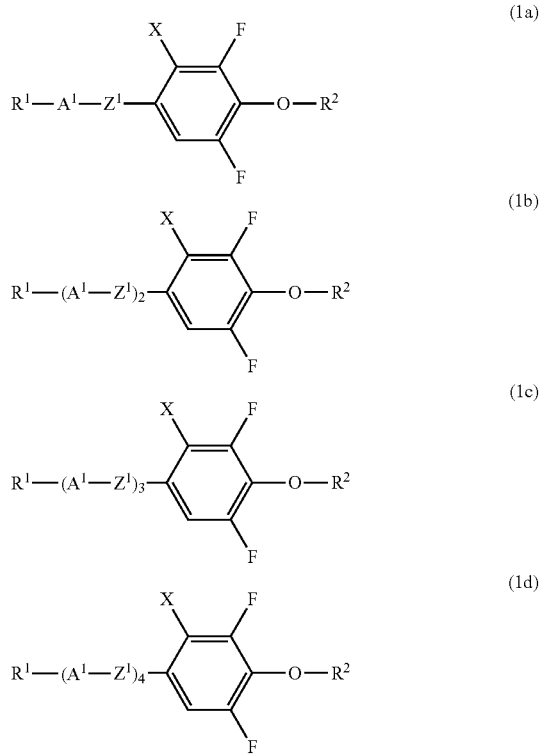

(In the formula, $R^1$, $A^1$, $Z^1$, X and $R^2$ each independently represent the same meaning as those of $R^1$, $A^1$, $Z^1$, X and $R^2$ of the general formula (1). However, in general formula (1b) to general formula (1d), at least one of $A^1$ groups represents 1,4-phenylene group or naphthalene-2,6-diyl group.)

The compound represented by general formula (1a) can be more preferably selected from general formula (1a-1) to general formula (1a-12).

[Formula 10]

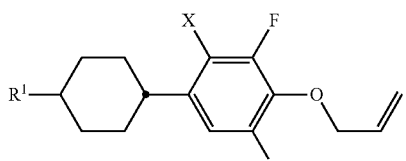
(1a-1)

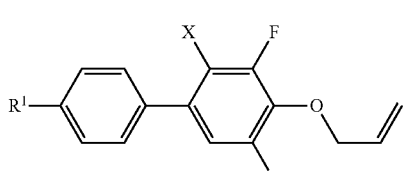
(1a-2)

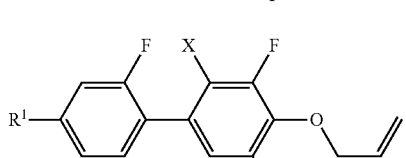
(1a-3)

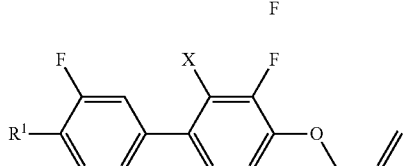
(1a-4)

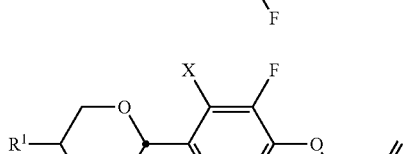
(1a-5)

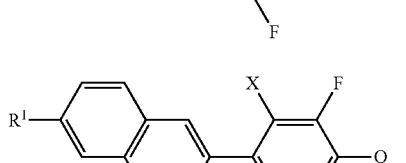
(1a-6)

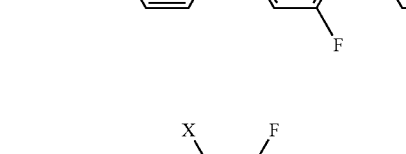
(1a-7)

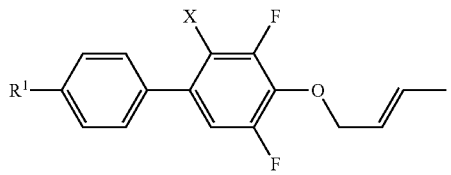
(1a-8)

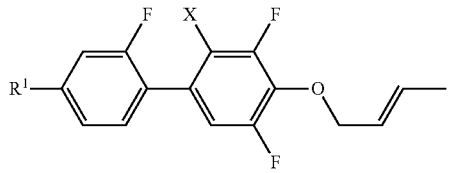
(1a-9)

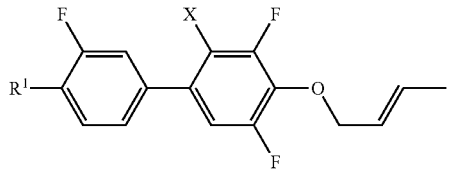
(1a-10)

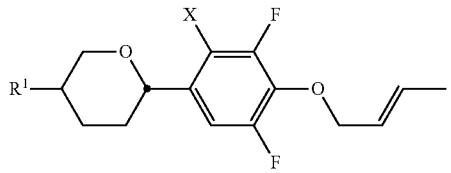
(1a-11)

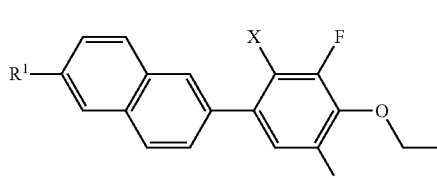
(1a-12)

(In the formula, $R^1$ and X each independently represent the same meaning as those of $R^1$ and X of the general formula (1).)

The compound represented by general formula (1b) can be more preferably selected from general formula (1b-1) to general formula (1b-34).

[Formula 11]

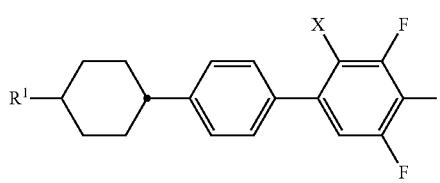
(1b-1)

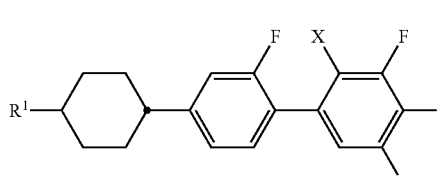
(1b-2)

-continued
(1b-3)
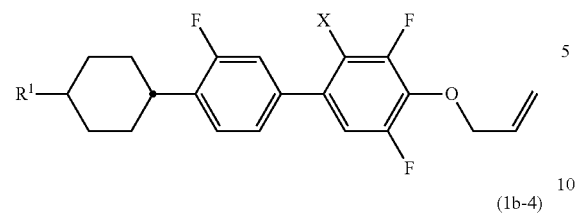
(1b-4)
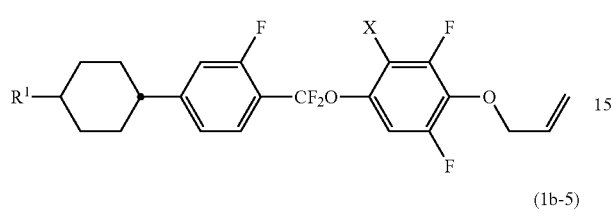
(1b-5)
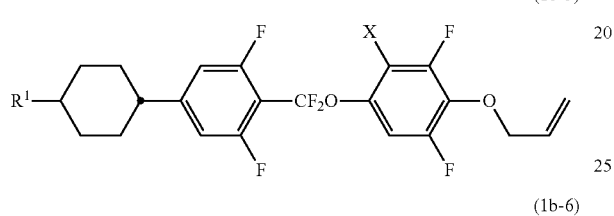
(1b-6)
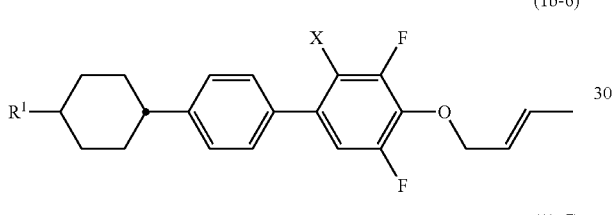
(1b-7)
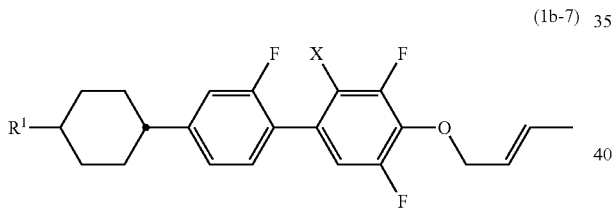
(1b-8)
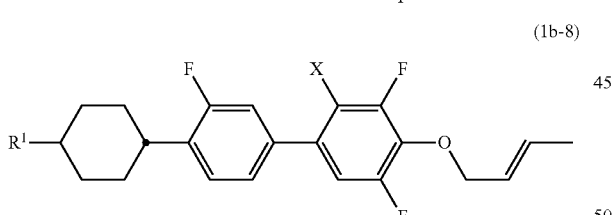
(1b-9)
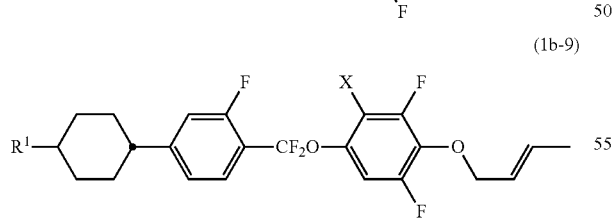
(1b-10)
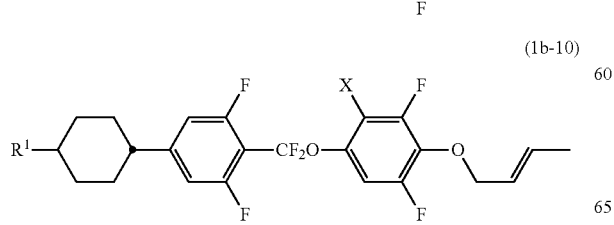
-continued
[Formula 12]
(1b-11)
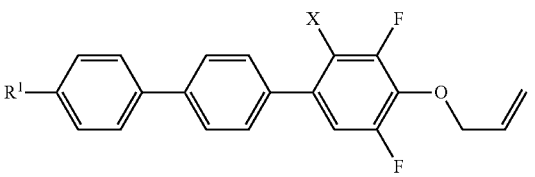
(1b-12)
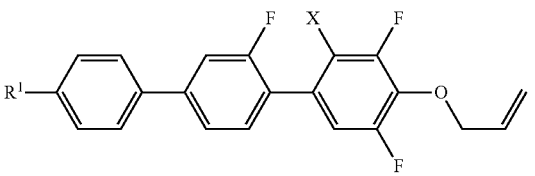
(1b-13)
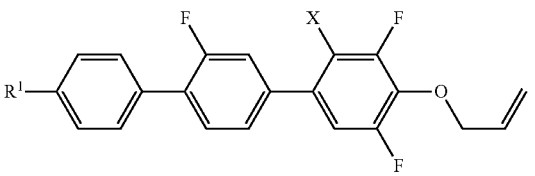
(1b-14)
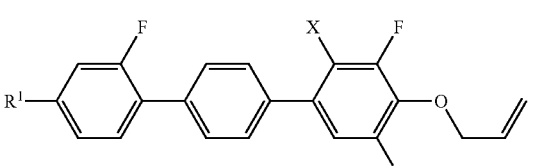
(1b-15)
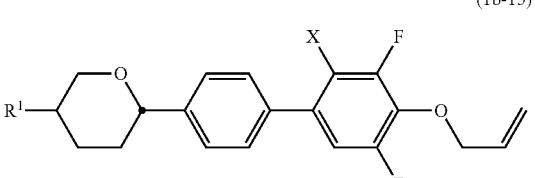
(1b-16)
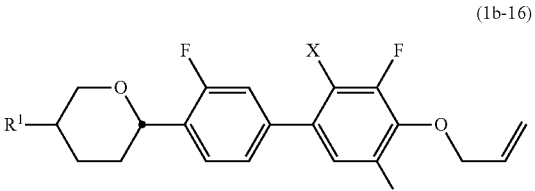
(1b-17)
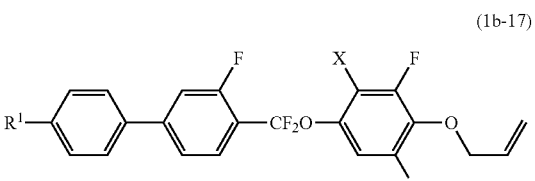
(1b-18)
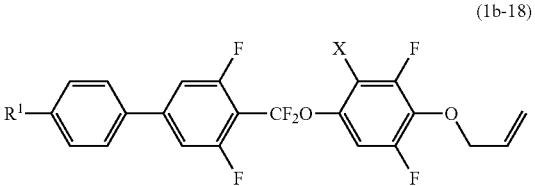

(1b-19)
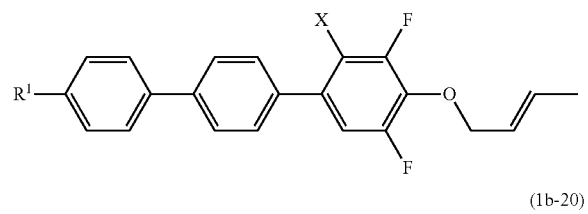
(1b-20)
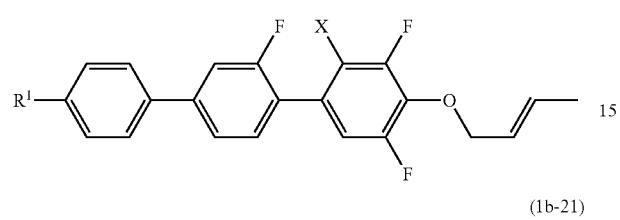
(1b-21)
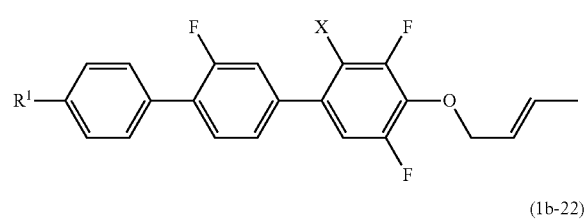
(1b-22)
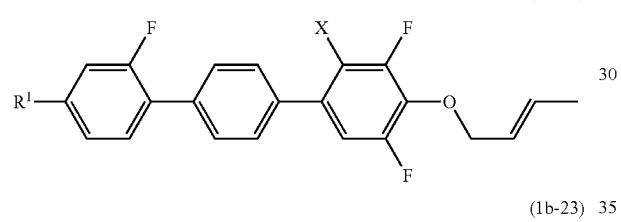
(1b-23)
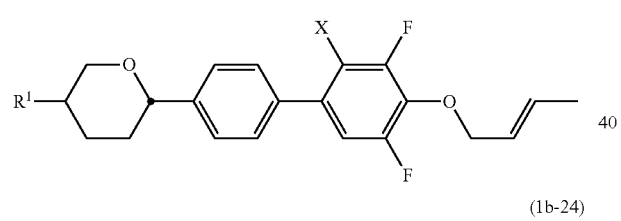
(1b-24)
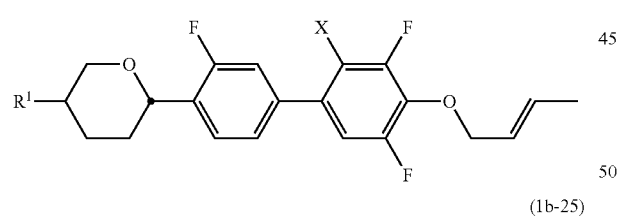
(1b-25)
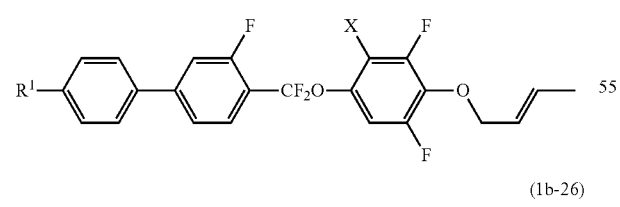
(1b-26)
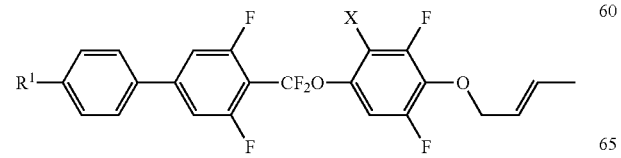
[Formula 13]
(1b-27)
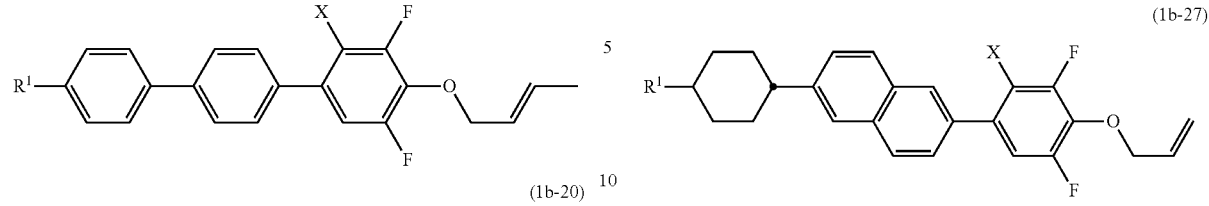
(1b-28)
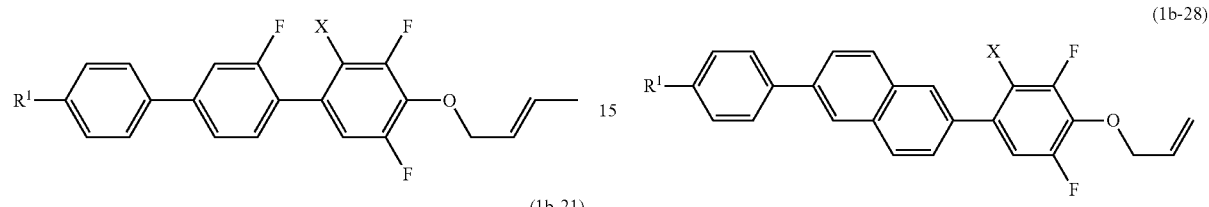
(1b-29)
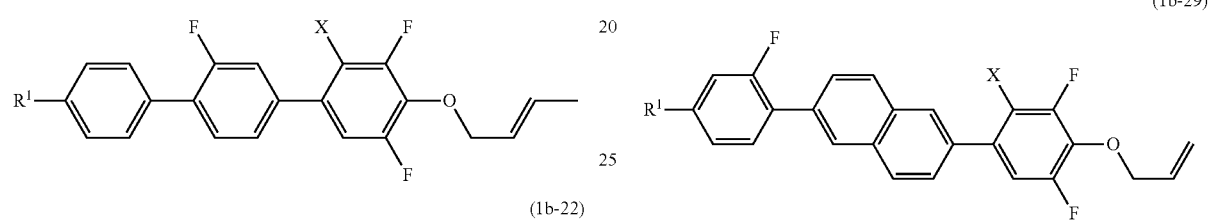
(1b-30)
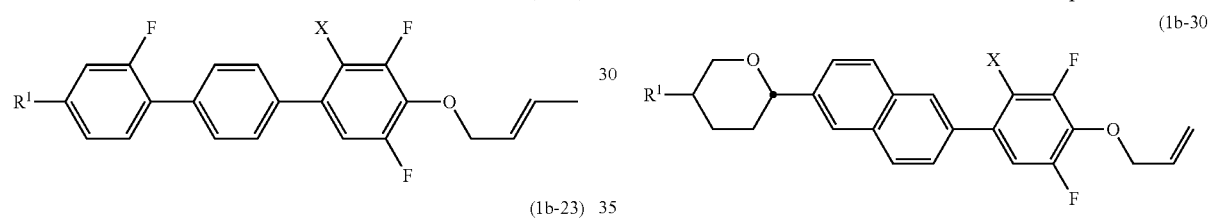
(1b-31)
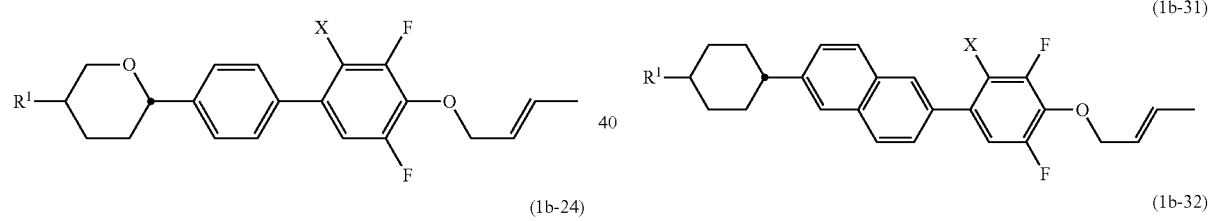
(1b-32)
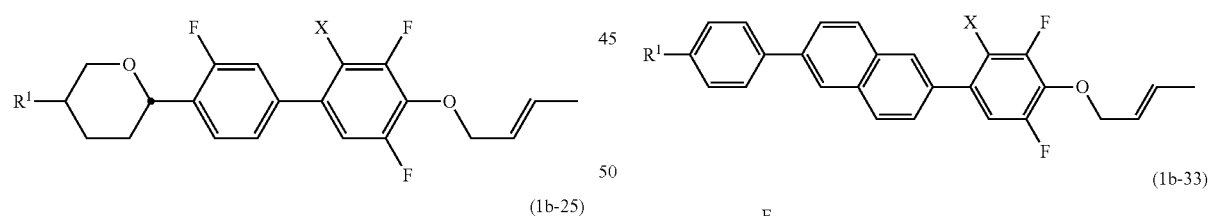
(1b-33)
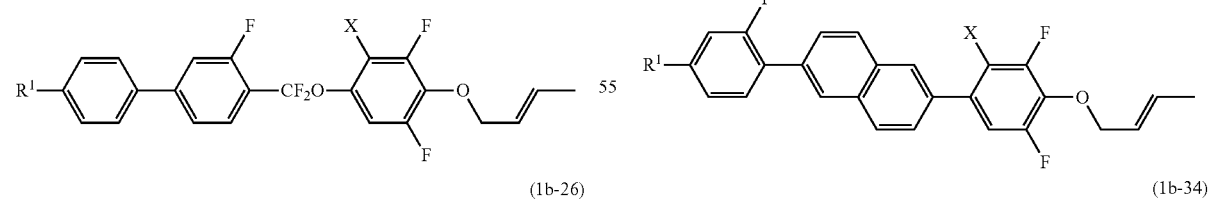
(1b-34)
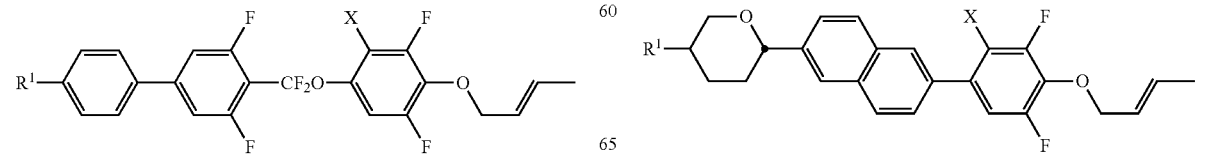

(In the formula, $R^1$ and X each independently represent the same meaning as those of $R^1$ and X of the general formula (1).)
The compound represented by general formula (1c) can be more preferably selected from general formula (1c-1) to general formula (1c-30).
[Formula 14]
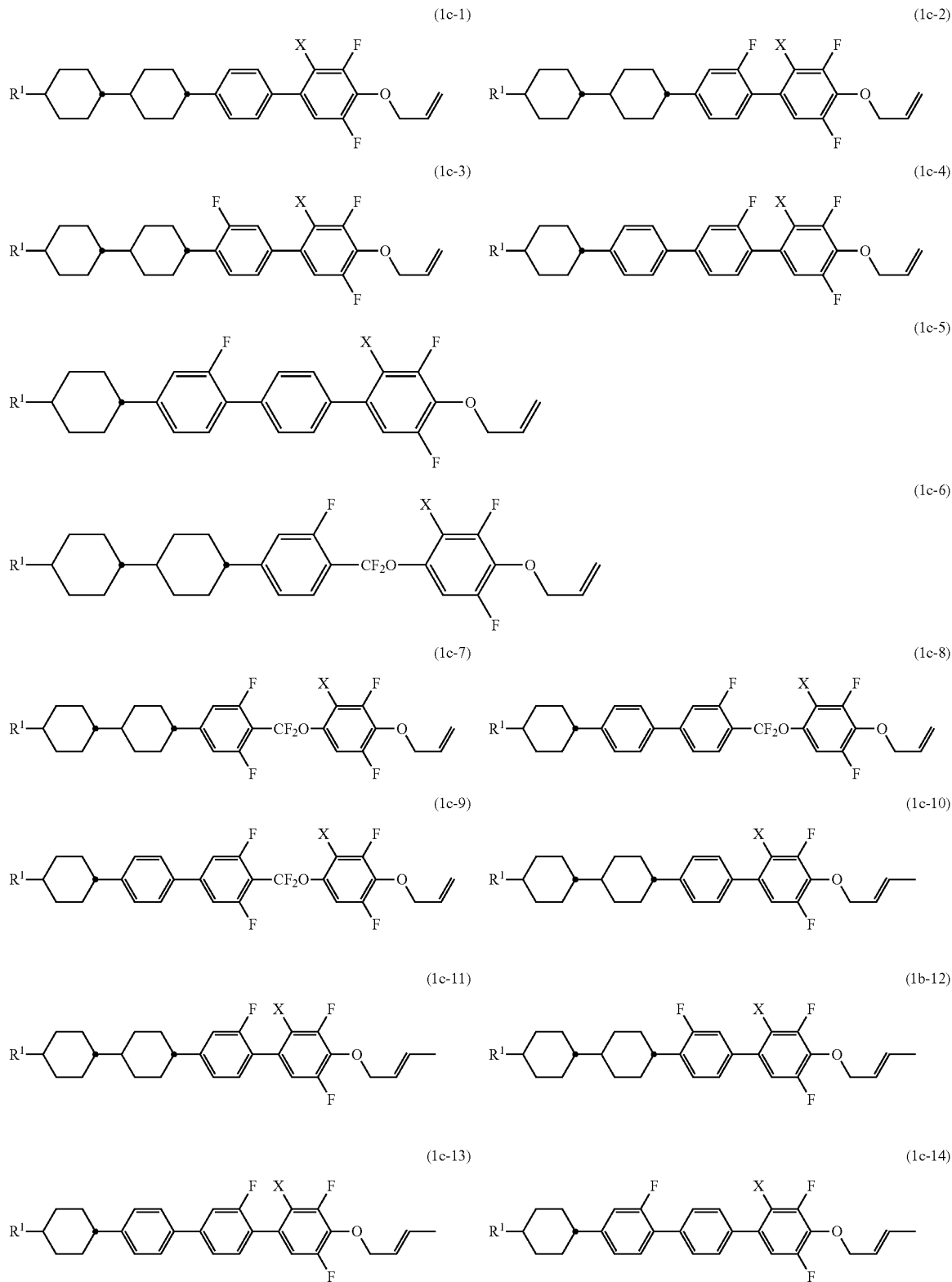

-continued
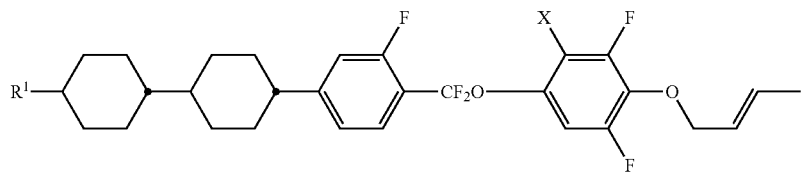
(1c-15)
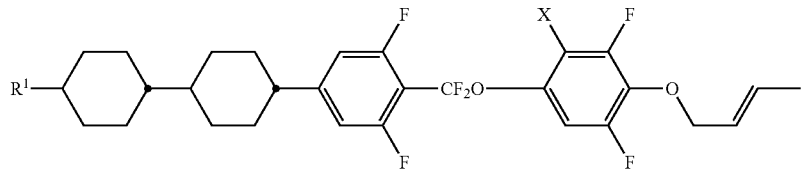
(1c-16)
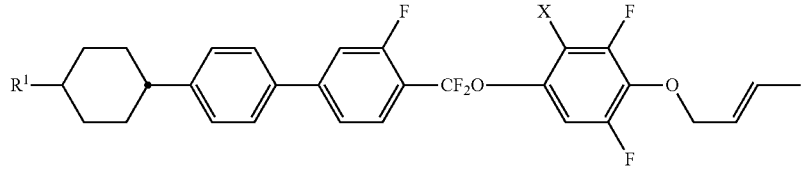
(1c-17)
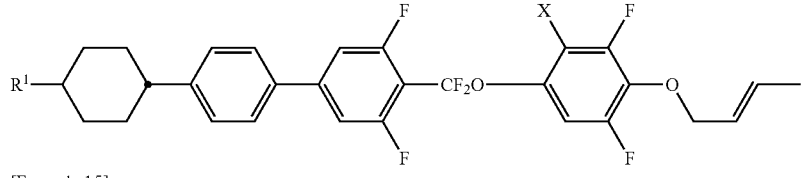
(1c-18)
[Formula 15]
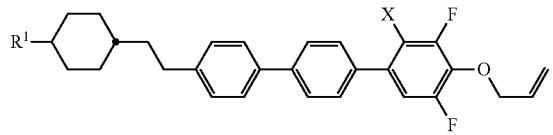
(1c-19)
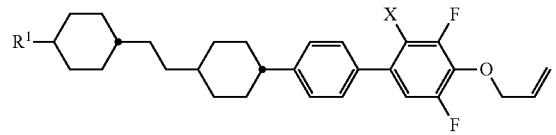
(1c-20)
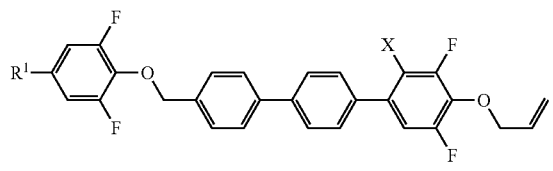
(1c-21)
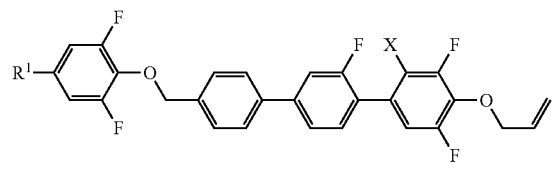
(1c-22)
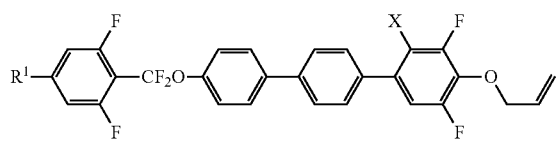
(1c-23)
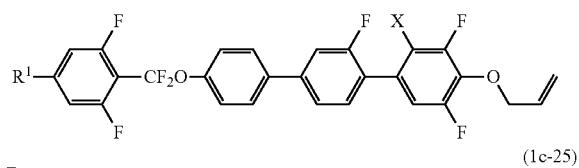
(1c-24)
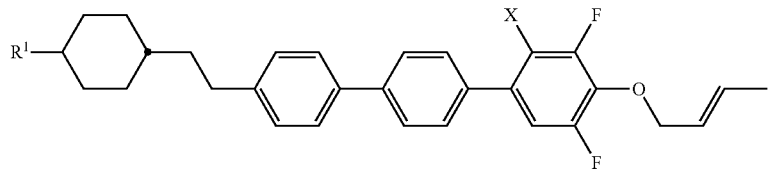
(1c-25)
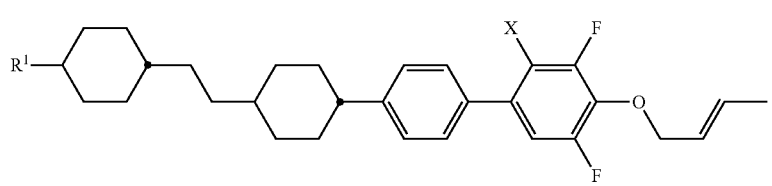
(1c-26)

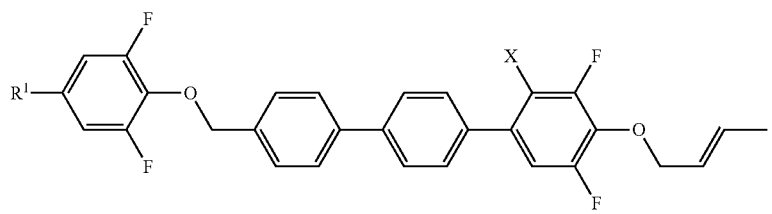
(1c-27)
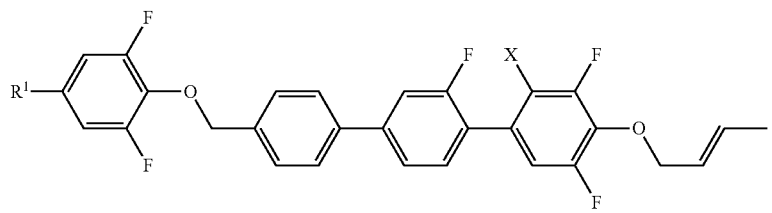
(1c-28)
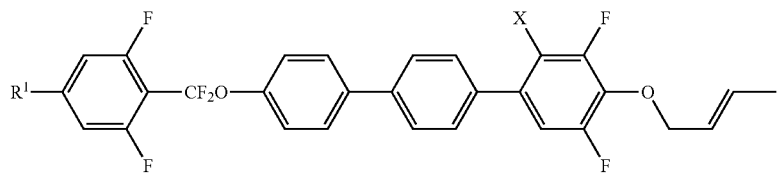
(1c-29)
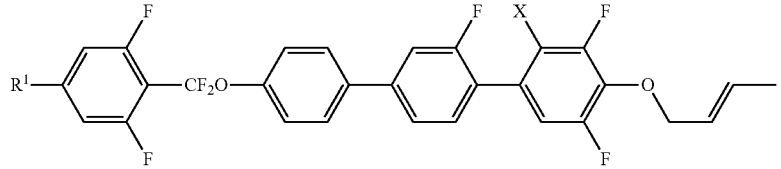
(1c-30)
(In the formula, $R^1$ and X each independently represent the same meaning as those of $R^1$ and X of the general formula (1).)
The compound represented by general formula (1d) can be more preferably selected from general formula (1d-1) to general formula (1d-24).
[Formula 16]
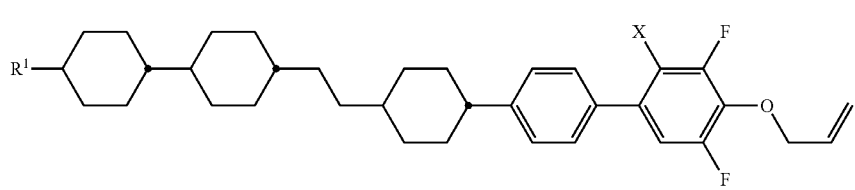
(1d-1)
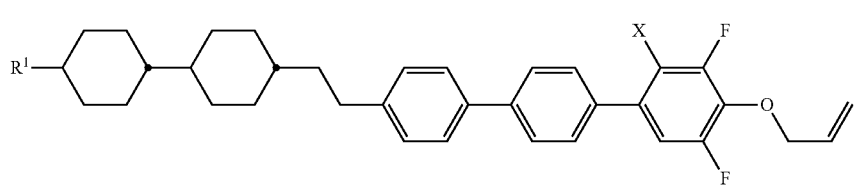
(1d-2)
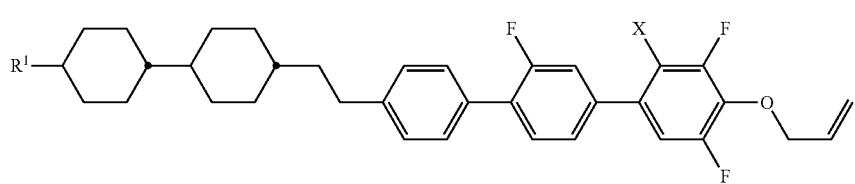
(1d-3)

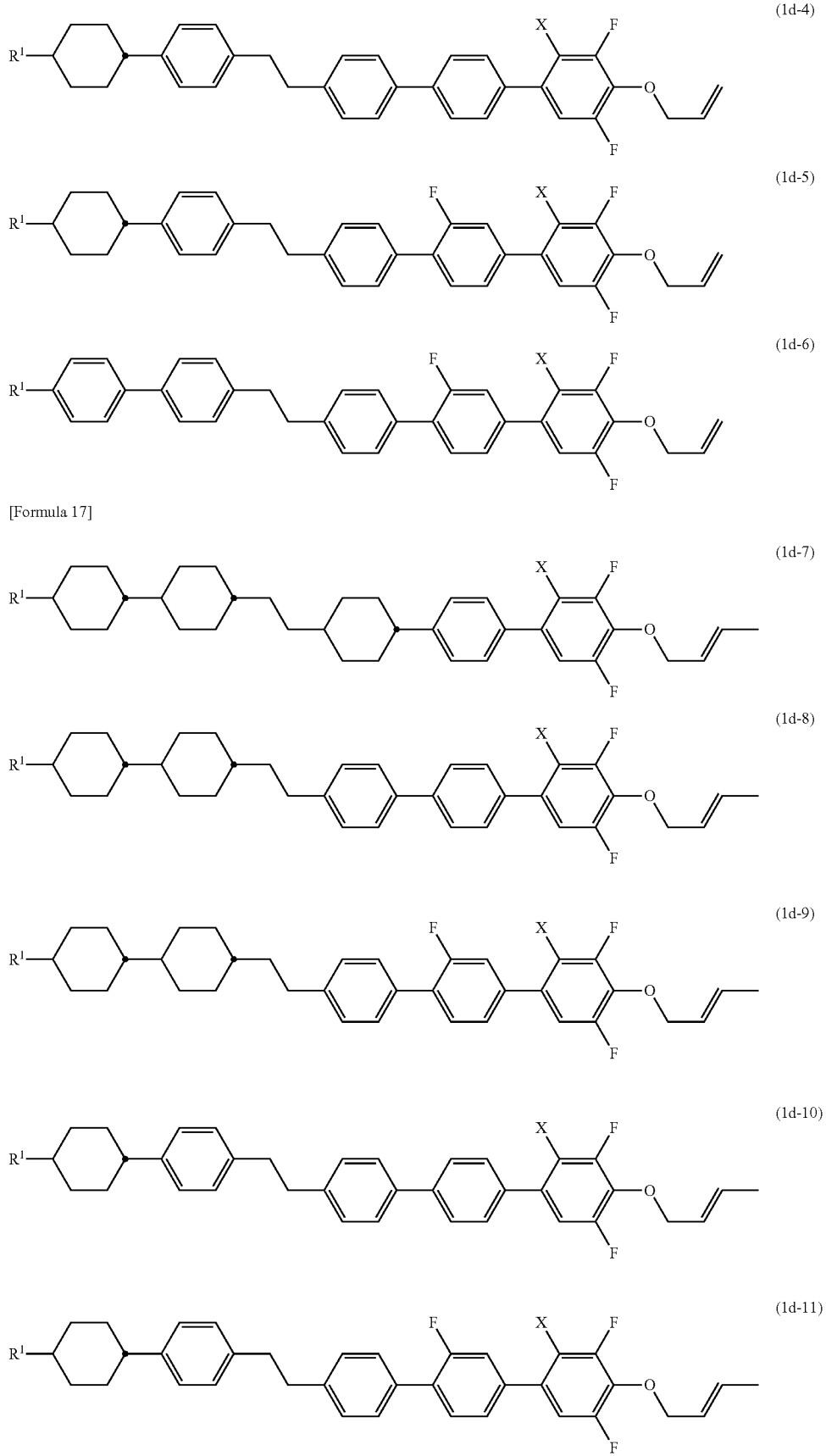

-continued
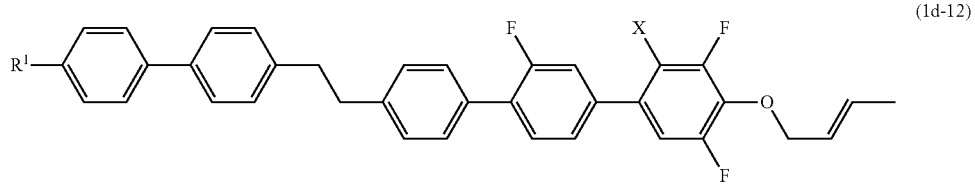
(1d-12)
[Formula 18]
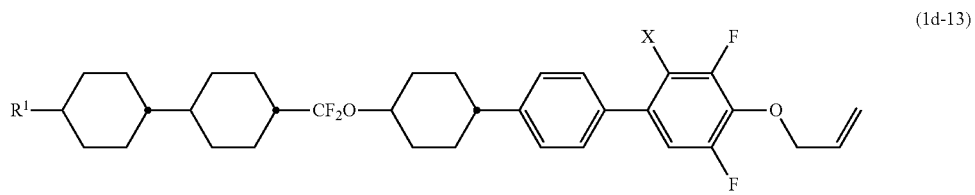
(1d-13)
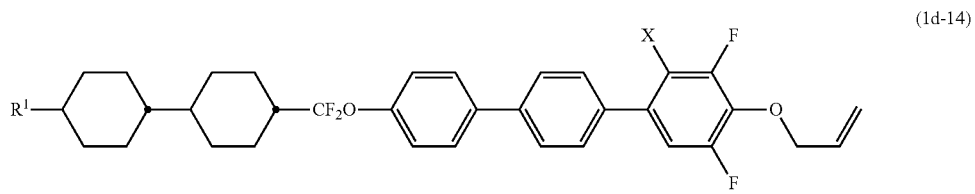
(1d-14)
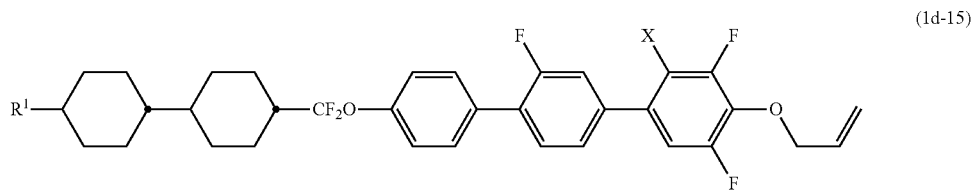
(1d-15)
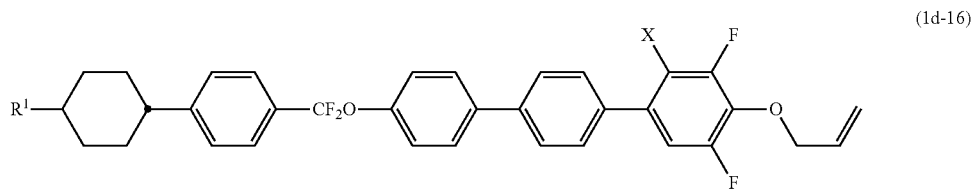
(1d-16)
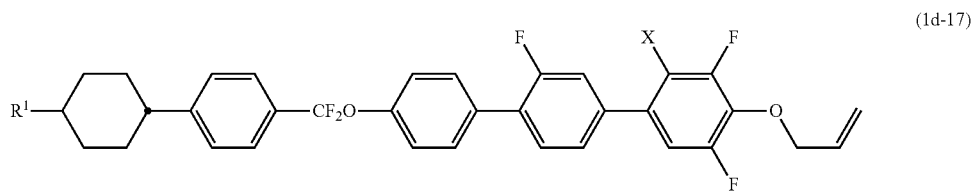
(1d-17)
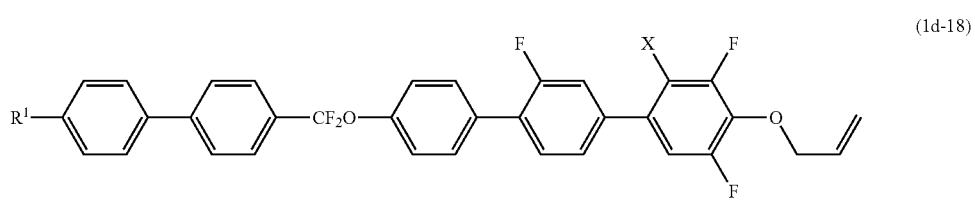
(1d-18)
[Formula 19]
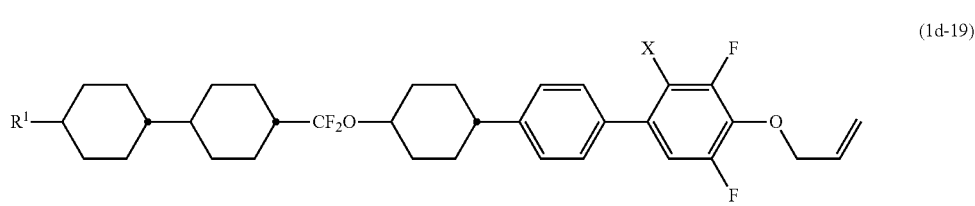
(1d-19)

-continued

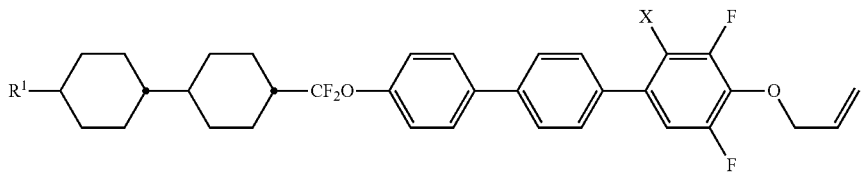
(1d-20)

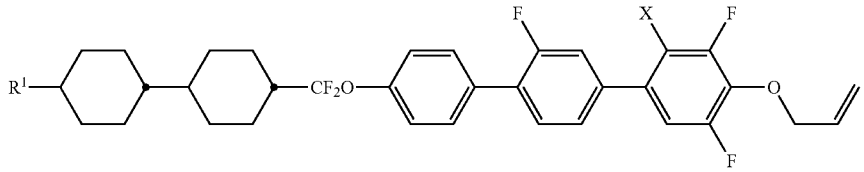
(1d-21)

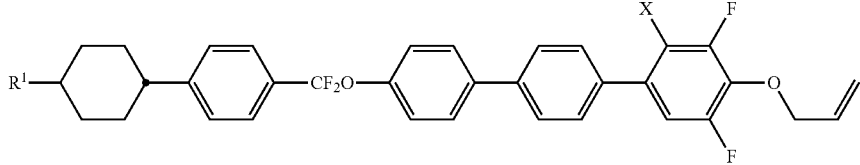
(1d-22)

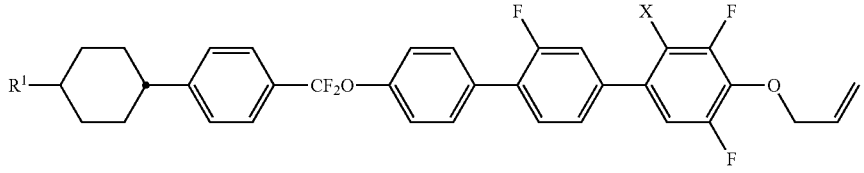
(1d-23)

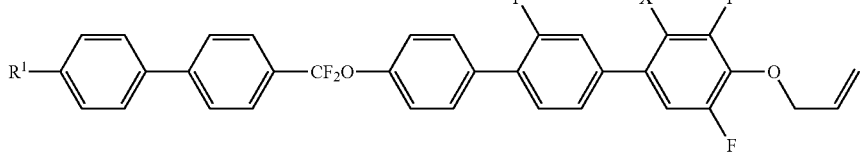
(1d-24)

(In the formula, $R^1$ and X each independently represent the same meaning as those of $R^1$ and X of the general formula (1).)

When the content of the compound represented by general formula (1) in the liquid crystal composition of the present invention is not enough, its effect does not appear. Therefore, its lower limit included in the composition is preferably 1 mass % or more (hereinafter, % in the composition means mass %.), and more preferably 2% or more, and yet more preferably 5% or more, and further more preferably at 10% or more. In addition, if its content is too much, a problem such as deposition can be caused. Therefore, its upper limit to be included therein is preferably 70% or less, more preferably 60% or less, and yet more preferably 50% or less, and further more preferably 40% or less. The compound represented by general formula (1) can be used alone or in combination of two or more compounds thereof.

The other compounds than the compound represented by general formula (1) can be used to adjust the physical properties of the liquid crystal composition. In addition to a compound having a liquid crystal phase, another compound which does not have a liquid crystal phase can be added, if necessary.

In this case, a typical example of a compound which can be mixed with the compound represented by general formula (1) can preferably include, in the composition of the present invention, at least one kind of the compound represented by general formula (1) as a first component, and at least one kind of the compounds selected from the second to the fourth component as other components.

Namely, the second component is so-called a p-type liquid crystal compound having a positive dielectric anisotropy, and can be exemplified as the compounds represented by general formula (LC1) and general formula (LC2).

[Formula 20]

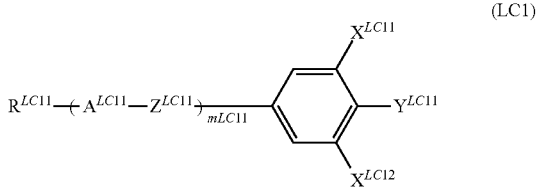
(LC1)

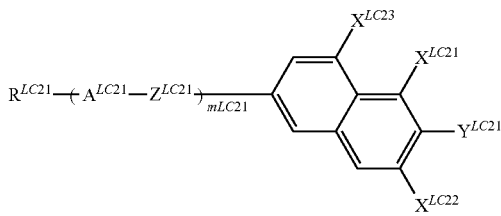

(LC2)

(in the formula, $R^{LC11}$ and $R^{LC21}$ each independently represent an alkyl group having a carbon atom number of 1 to 15, in which one or two or more of the $CH_2$ groups in the alkyl group can be substituted with —O—, —CH=CH—, —CO—, —OCO—, —COO— or —C≡C— without being directly adjacent to an oxygen atom, in which one or two or more of the hydrogen atoms in the alkyl group can be optionally substituted with a halogen atom; and $A^{LC11}$ and $A^{LC21}$ are each independently have one of the structures below:

[Formula 21]

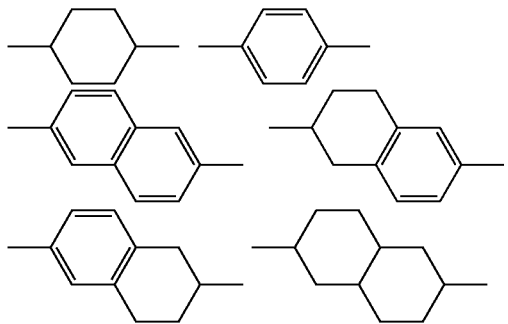

(in the structure, one or two or more of the —$CH_2$— groups in the cyclohexylene group can be replaced with an oxygen atom; one or two or more of the —CH— groups in the 1,4-phenylene group can be replaced with a nitrogen atom: and one or two or more of the hydrogen atoms in the structure can be substituted with a fluorine atom, a chlorine atom, —$CF_3$ or —$OCF_3$.); $X^{LC11}$, $X^{LC12}$, and $X^{LC21}$ to $X^{LC23}$ each independently represent a hydrogen atom, fluorine atom, chlorine atom, —$CF_3$ or —$OCF_3$; $Y^{LC11}$ and $Y^{LC21}$ each independently represent a hydrogen atom, fluorine atom, chlorine atom, cyano group, —$CF_3$, —$OCH_2F$, —$OCHF_2$ or —$OCF_3$; $Z^{LC11}$ and $Z^{LC21}$ each independently represent a single bond, —CH=CH—, —CF=CF—, —C≡C—, —$CH_2CH_2$—, —$(CH_2)_4$—, —$OCH_2$—, —$CH_2O$—, —$OCF_2$—, —$CF_2O$—, —COO— or —OCO—; $m^{LC11}$ and $m^{LC21}$ each independently represent an integer of 1 to 4; when plural $A^{LC11}$, $A^{LC21}$, $Z^{LC11}$ and $Z^{LC21}$ exist, they can be the same as or different from each other.);

it is preferable that $R^{LC11}$ and $R^{LC21}$ are each independently an alkyl group having a carbon atom number of 1 to 7, an alkoxy group having a carbon atom number of 1 to 7, or an alkenyl group having a carbon atom number of 2 to 7; it is more preferable that $R^{LC11}$ and $R^{LC21}$ are each independently an alkyl group having a carbon atom number of 1 to 5, an alkoxy group having a carbon atom number of 1 to 5, an alkenyl group having a carbon atom number of 2 to 5; it is further preferable that they are of a straight chain; it is most preferable that the alkenyl group has one of the structures below.

[Formula 22]

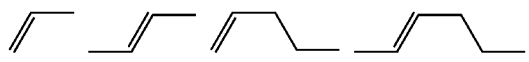

(the right side end of the structure in the formula above shall be combined to the ring structure.)

It is preferable that $A^{LC11}$ and $A^{LC21}$ each independently have one of the structures below.

[Formula 23]

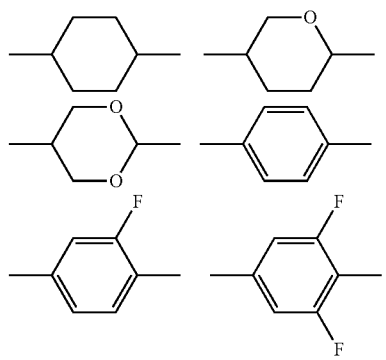

It is preferable that $Y^{LC11}$ and $Y^{LC21}$ each independently represent a fluorine atom, cyano group, —$CF_3$ or —$OCF^3$; and more preferable that they each independently represent a fluorine atom or —$OCF_3$; and particularly preferable that they each independently represent a fluorine atom.

It is preferable that $Z^{LC11}$ and $Z^{LC21}$ represent a single bond, —$CH_2CH_2$—, —COO—, —OCO—, —$OCH_2$—, —$CH_2O$—, —$OCF_2$— or —$CF_2O$—; and more preferable that they represent a single bond, —$CH_2CH_2$—, —$OCH_2$—, —$OCF_2$— or —$CF_2O$—; and particularly preferable that they represent a single bond. —$OCH_2$— or —$CF_2O$—.

It is preferable that $m^{LC11}$ and $m^{LC21}$ represent 1. 2 or 3. When the preservation stability at the low temperature and the response speed are given weight, they are preferable to be 1 or 2. They are preferable to be 2 or 3 in order to improve an upper limit of the nematic phase upper limit temperature.

The general formula (LC1) can be preferably selected from one kind or two or more kinds of the compounds represented by general formula (LC1-a) to general formula (LC1-c).

[Formula 24]

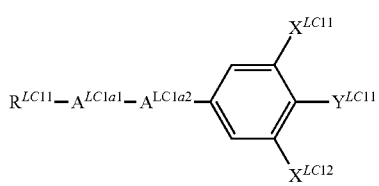

(LC1-a)

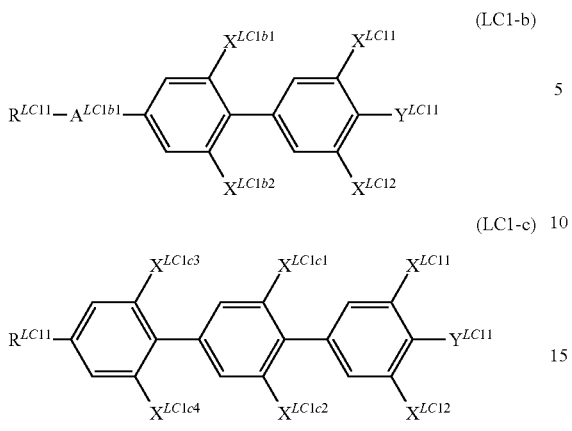

(LC1-b)

(LC1-c)

(In the formula, $R^{LC11}$, $Y^{LC11}$, $X^{LC11}$ and $X^{LC12}$ each independently represent the same meaning as those of $R^{LC11}$, $Y^{LC11}$, $X^{LC11}$ and $X^{LC12}$ of the general formula (LC1); $A^{LC1a1}$, $A^{LC1a2}$ and $A^{LC1b1}$ represent trans-1,4-cyclohexylene group, tetrahydropyran-2,5-diyl group, or 1,3-dioxane-2,5-diyl group; $X^{LC1b1}$, $X^{LC1b2}$, and $X^{LC1c1}$ to $X^{LC1c4}$ each independently represent a hydrogen atom, fluorine atom, chlorine atom, —$CF_3$ or —$OCF_3$.).

It is preferable that $R^{LC11}$ is each independently an alkyl group having a carbon atom number of 1 to 7, an alkoxy group having a carbon atom number of 1 to 7, or an alkenyl group having a carbon atom number of 2 to 7; and it is more preferable that $R^{LC11}$ is each independently an alkyl group having a carbon atom number of 1 to 5, an alkoxy group having a carbon atom number of 1 to 5, or an alkenyl group having a carbon atom number of 2 to 5.

It is preferable that $X^{LC11}$ to $X_{LC1c4}$ are each independently a hydrogen atom or fluorine atom.

It is preferable that $Y^{LC11}$ is each independently a fluorine atom, —$CF_3$ or —$OCF_3$.

The general formula (LC1) can be preferably selected from one kind or two or more kinds of the compounds represented by general formula (LC1-d) to general formula (LC1-m).

[Formula 25]

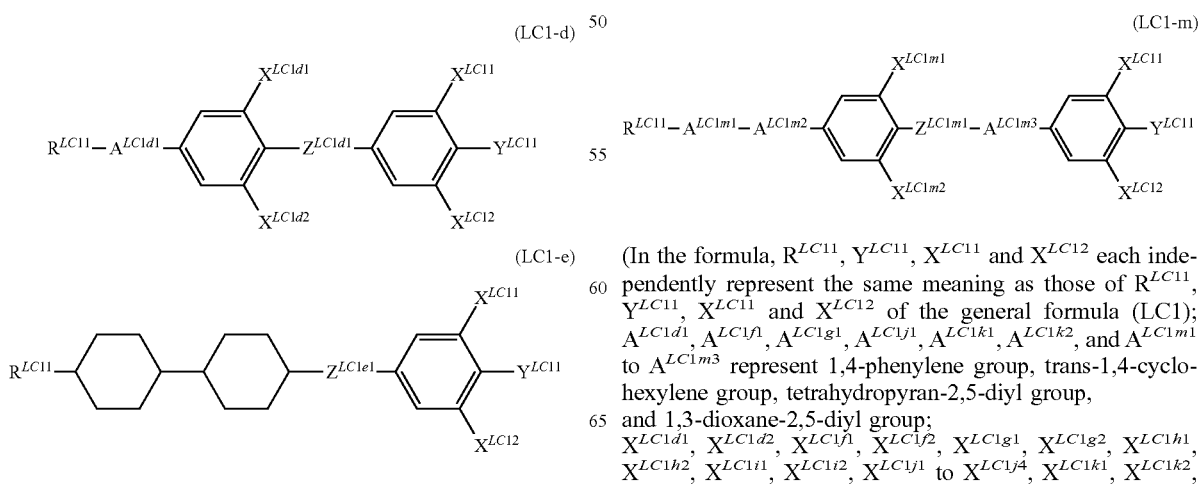

(In the formula, $R^{LC11}$, $Y^{LC11}$, $X^{LC11}$ and $X^{LC12}$ each independently represent the same meaning as those of $R^{LC11}$, $Y^{LC11}$, $X^{LC11}$ and $X^{LC12}$ of the general formula (LC1); $A^{LC1d1}$, $A^{LC1f1}$, $A^{LC1g1}$, $A^{LC1j1}$, $A^{LC1k1}$, $A^{LC1k2}$, and $A^{LC1m1}$ to $A^{LC1m3}$ represent 1,4-phenylene group, trans-1,4-cyclohexylene group, tetrahydropyran-2,5-diyl group, and 1,3-dioxane-2,5-diyl group; $X^{LC1d1}$, $X^{LC1d2}$, $X^{LC1f1}$, $X^{LC1f2}$, $X^{LC1g1}$, $X^{LC1g2}$, $X^{LC1h1}$, $X^{LC1h2}$, $X^{LC1i1}$, $X^{LC1i2}$, $X^{LC1j1}$ to $X^{LC1j4}$, $X^{LC1k1}$, $X^{LC1k2}$, $X^{LC1m1}$, and $X^{LC1m2}$ each independently represent a hydrogen atom, fluorine atom, chlorine atom, —CF$_3$ or —OCF$_3$; and $Z^{LC1d1}$, $Z^{LC1e1}$, $Z^{LC1j1}$, $Z^{LC1k1}$ and $Z^{LC1m1}$ each independently represent a single bond, —CH=CH—, —CF=CF—, □≡CH$_2$CH$_2$—, —(CH$_2$)$_4$—, —OCH$_2$—, —CH$_2$O—, —OCF$_2$—, —CF$_2$O—, —COO— or —OCO—.)

It is preferable that $X^{LC11}$ to $X_{LC1m}{}^2$ are each independently a hydrogen atom or fluorine atom.

It is preferable that $Y^{LC11}$ is each independently a fluorine atom, —CF$_3$ or —OCF$_3$.

It is preferable that $Z^{LC1d1}$ to $Z^{LC1m1}$ each independently represent —CF$_2$O— or —OCH$_2$—. The general formula (LC2) can be preferably selected from one kind or two or more kinds of the compounds represented by general formula (LC2-a) to general formula (LC2-g).

[Formula 26]

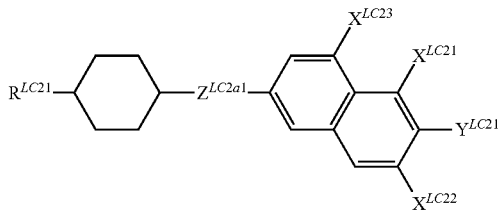 (LC2-a)

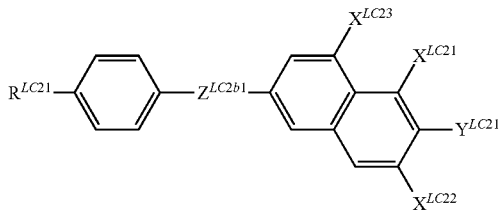 (LC2-b)

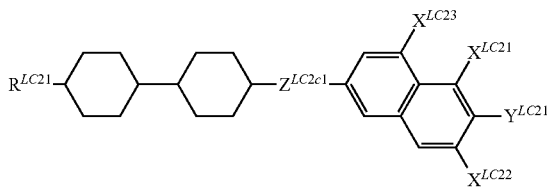 (LC2-c)

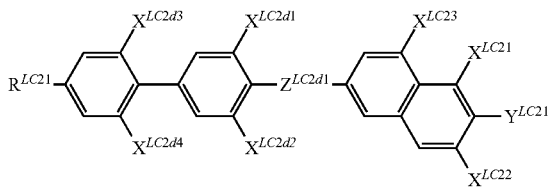 (LC2-d)

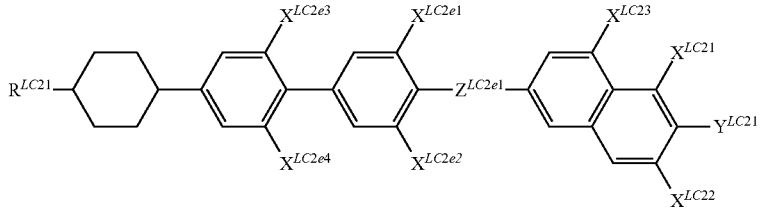 (LC2-e)

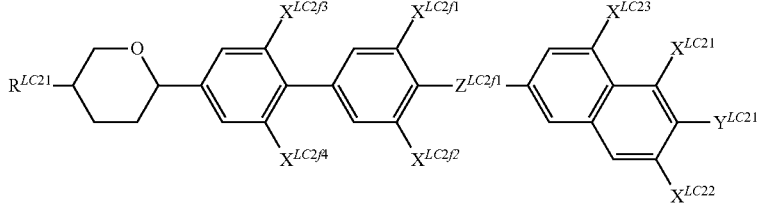 (LC2-f)

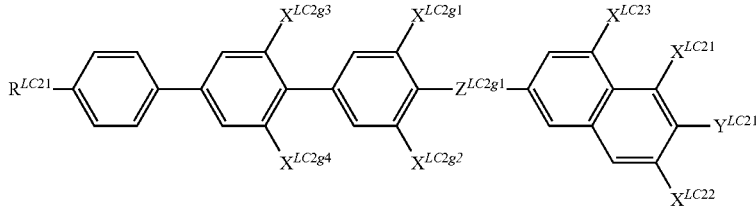 (LC2-g)

It is preferable that $R^{LC11}$ is each independently an alkyl group having a carbon atom number of 1 to 7, an alkoxy group having a carbon atom number of 1 to 7, or an alkenyl group having a carbon atom number of 2 to 7; and it is more preferable that $R^{LC11}$ is each independently an alkyl group having a carbon atom number of 1 to 5, an alkoxy group having a carbon atom number of 1 to 5, or an alkenyl group having a carbon atom number of 2 to 5.

(In the formula, $R^{LC21}$, $Y^{LC21}$, and $X^{LC21}$ to $X^{LC23}$ each independently represent the same meanings as those of $R^{LC21}$, $Y^{LC21}$, and $X^{LC21}$ to $X^{LC23}$ of the general formula (LC2);

$X^{LC2d1}$ to $X^{LC2d4}$, $X^{LC2e1}$ to $X^{LC2e4}$, $X^{LC2f1}$ to $X^{LC2f4}$, and $X^{LC2g1}$ to $X^{LC2g4}$ each independently represent a hydrogen atom, fluorine atom, chlorine atom, —CF$_3$ or —OCF$_3$;

and $Z^{LC2a1}$, $Z^{LC2b1}$, $Z^{LC2c1}$, $Z^{LC2d1}$, $Z^{LC2e1}$, $Z^{LC2f1}$ and $Z^{LC2g1}$ each independently represent a single bond, —CH=CH—, —CF=CF—, —C≡C—, —CH$_2$CH—, —(CH$_2$)$_4$—, —OCH$_2$—, —CH$_2$O—, —OCF$_2$—, —CF$_2$O—, —COO— or —OCO—.

It is preferable that $R^{LC21}$ is each independently an alkyl group having a carbon atom number of 1 to 7, an alkoxy group having a carbon atom number of 1 to 7, or an alkenyl group having a carbon atom number of 2 to 7; and it is more preferable that $R^{LC21}$ is each independently an alkyl group having a carbon atom number of 1 to 5, an alkoxy group having a carbon atom number of 1 to 5, or an alkenyl group having a carbon atom number of 2 to 5.

It is preferable that $X^{LC21}$ to $X^{LC2g4}$ each independently represent a hydrogen atom or fluorine atom, and it is preferable that $Y^{LC21}$ each independently represents a fluorine atom, —CF$_3$ or —OCF$_3$.

It is preferable that $Z^{LC2a1}$ to $Z^{LC2g4}$ each independently represent —CF$_2$O— or —OCH$_2$—.

The third component is so-called an n-type liquid crystal compound having a negative dielectric anisotropy, and can be exemplified as the compounds represented by general formula (LC3) and general formula (LC5).

[Formula 27]

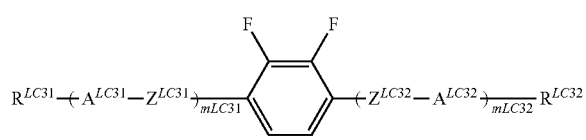
(LC3)

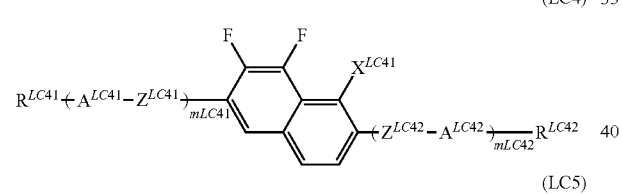
(LC4)

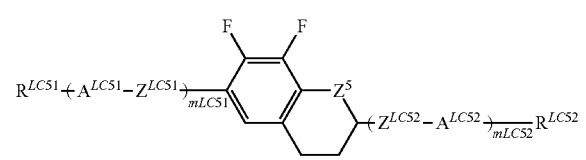
(LC5)

(In the formula, $R^{LC31}$, $R^{LC32}$, $R^{LC41}$, $R^{LC42}$, $R^{LC51}$ and $R^{LC52}$ each independently represent an alkyl group having a carbon atom number of 1 to 15; in which one or two or more of the CH$_2$ groups in the alkyl group can be substituted with —O—, —CH=CH—, —CO—, —OCO—, —COO— or —C≡C— without being directly adjacent to an oxygen atom, in which one or two or more of the hydrogen atoms in the alkyl group can be optionally substituted with a halogen atom; and $A^{LC31}$, $A^{LC32}$, $A^{LC41}$, $A^{LC42}$, $A^{LC51}$ and $A^{LC52}$ each independently have one of the structures below.

[Formula 28]

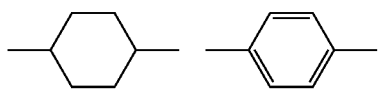

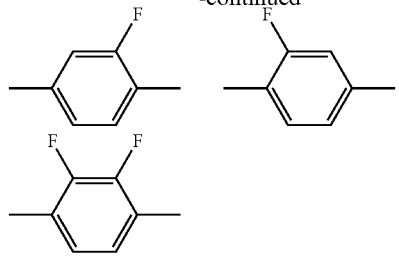

(in the structure, one or two or more of the —CH$_2$— groups in the cyclohexylene group can be replaced with an oxygen atom; one or two or more of the —CH— groups in the 1,4-phenylene group can be replaced with a nitrogen atom; and one or two or more of the hydrogen atoms in the structure can be substituted with a fluorine atom, chlorine atom, —CF$_3$ or —OCF$_3$.);

$Z^{LC31}$, $Z^{LC32}$, $Z^{LC41}$, $Z^{LC42}$, $Z^{LC51}$ and $Z^{LC51}$ each independently represent a single bond, —CH=CH—, —C≡C—, —CH$_2$CH$_2$—, —(CH$_2$)$_4$—, —COO—, —OCH$_2$—, —CH$_2$O—, —OCF$_2$— or —CF$_2$O—;

$Z^5$ represents —CH$_2$— or an oxygen atom, and $X^{LC41}$ represents a hydrogen atom or fluorine atom;

$m^{LC31}$, $m^{LC32}$, $m^{LC41}$, $m^{LC42}$, $m^{LC51}$ and $m^{LC52}$ each independently represent 0 to 3;

$m^{LC31}+m^{LC32}$, $m^{LC41}+m^{LC42}$ and $m^{LC51}+m^{LC52}$ are 1, 2 or 3; and when a plural number of $A^{LC31}$ to $A^{LC52}$, and $Z^{LC31}$ to $Z^{LC52}$ exist, they can be the same as or different from each other.). It is preferable that $R^{LC31}$ and $R^{LC52}$ are each independently an alkyl group having a carbon atom number of 1 to 7, an alkoxy group having a carbon atom number of 1 to 7, or an alkenyl group having a carbon atom number of 2 to 7; and it is preferable that the alkenyl group has one of the structures below.

[Formula 29]

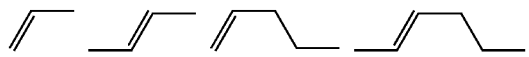

(the right side end of the structure in the formula above shall be combined to the ring structure.)

It is preferable that $A^{LC31}$ to $A^{LC52}$ each independently have one of the structures below.

[Formula 30]

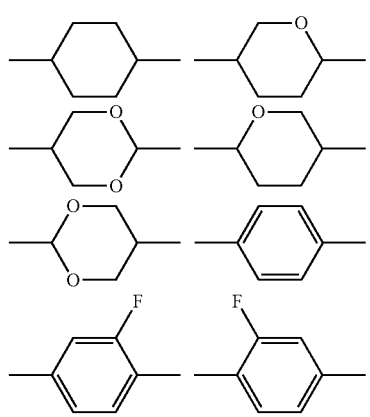

-continued

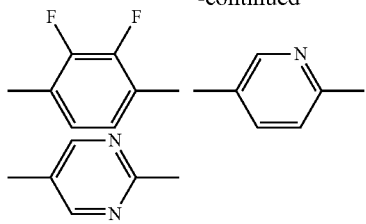

It is preferable that $Z^{LC31}$ to $Z^{LC51}$ each independently represent a single bond, —CH$_2$O—, —COO—, —OCO—, —CH$_2$CH$_2$—, —CF$_2$O—, —OCF$_2$— or —OCH$_2$—.

The general formula (LC3) can be preferably selected from one kind or two or more kinds of the compounds represented by general formula (LC3-a) to general formula (LC3-b).

[Formula 31]

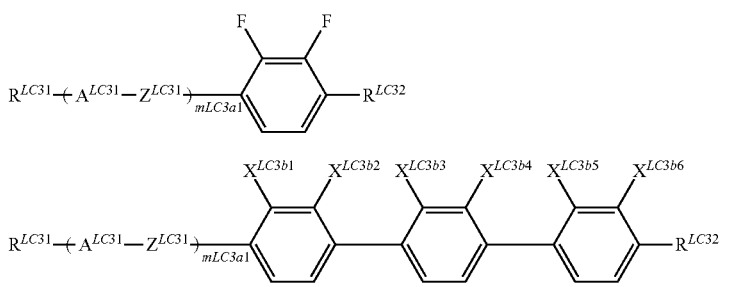

(LC3-a)

(LC3-b)

(In the formula, $R^{LC31}$, $R^{LC32}$, $A^{LC31}$ and $Z^{LC31}$ each independently represent the same meanings as those of $R^{LC31}$, $R^{LC32}$, $A^{LC31}$ and $Z^{LC31}$ of the general formula (LC3); $X^{LC3b1}$ to $X^{LC3b6}$ represent a hydrogen atom or fluorine atom, in which at least one combination of $X^{LC3b1}$ and $X^{LC3b2}$, or $X^{LC3b3}$ and $X^{LC3b4}$ both represents a fluorine atom; $m^{LC3a1}$ is 1, 2 or 3; $m^{LC3b1}$ represents 0 or 1; and when a plural number of $A^{LC31}$ and $Z^{LC31}$ exist, they are the same as or different from each other.).

It is preferable that $R^{LC31}$ and $R^{LC32}$ are each independently an alkyl group having a carbon atom number of 1 to 7, an alkoxy group having a carbon atom number of 1 to 7, an alkenyl group having a carbon atom number of 2 to 7, or an alkenyloxy group having a carbon atom number of 2 to 7.

It is preferable that $A^{LC31}$ represents 1,4-phenylene group, trans-1,4-cyclohexylene group, tetrahydropyran-2,5-diyl group, or 1,3-dioxane-2,5-diyl group; it is more preferable that it represents 1,4-phenylene group, or trans-1,4-cyclohexylene group.

It is preferable that $Z^{LC31}$ represents a single bond, —CH$_2$O—, —COO—, —OCO—, or —CH$_2$CH$_2$—; and it is more preferable that it represents a single bond.

It is preferable that the general formula (LC3-a) is specified as general formula (LC3-a1) to general formula (LC3-a4) below.

[Formula 32]

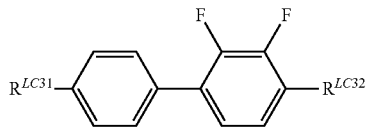

(LC3-a1)

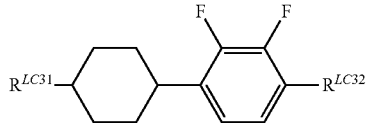

(LC3-a2)

-continued

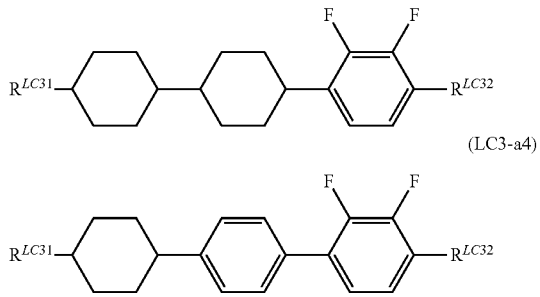

(LC3-a3)

(LC3-a4)

(In the formula, $R^{LC31}$ and $R^{LC32}$ each independently represent the same meanings as those of $R^{LC31}$ and $R^{LC32}$ of the general formula (LC3).)

It is preferable that $R^{LC31}$ and $R^{LC32}$ are each independently an alkyl group having a carbon atom number of 1 to 7, an alkoxy group having a carbon atom number of 1 to 7, or an alkenyl group having a carbon atom number of 2 to 7; and it is preferable that $R^{LC31}$ is an alkyl group having a carbon atom number of 1 to 7, and that $R^{LC32}$ is an alkoxy group having a carbon atom number of 1 to 7.

The general formula (LC3-b) is preferably specified as general formula (LC3-b1) to general formula (LC3-b12); and more preferably as general formula (LC3-b1), general formula (LC3-b6), general formula (LC3-b8), general formula (LC3-b11); and yet more preferably as general formula (LC3-b1) and general formula (LC3-b6); and most preferably as general formula (LC3-b1).

[Formula 33]

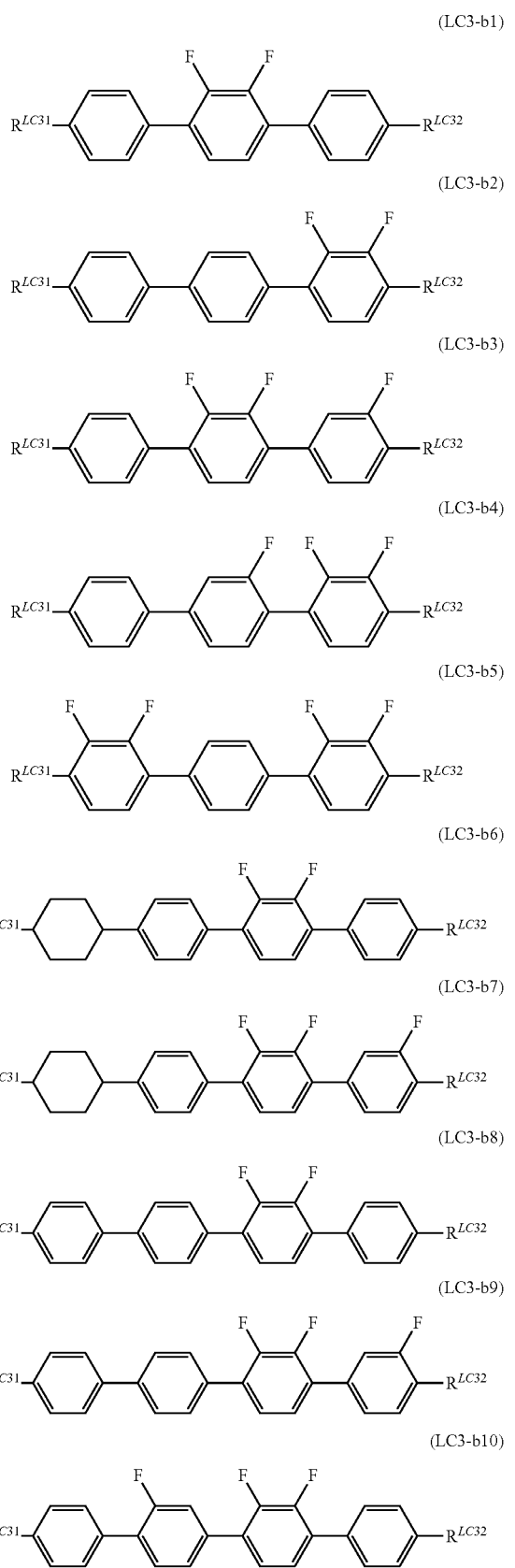

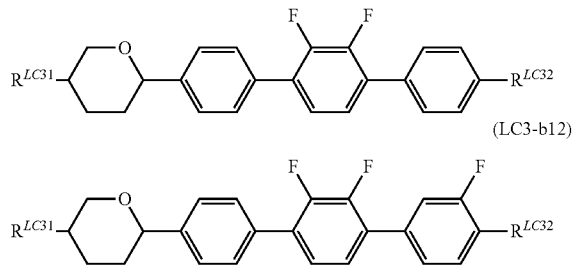

(In the formula, $R^{LC31}$ and $R^{LC32}$ each independently represent the same meanings as those of $R^{LC31}$ and $R^{LC32}$ of the general formula (LC3).)

It is preferable that $R^{LC31}$ and $R^{LC32}$ are each independently an alkyl group having a carbon atom number of 1 to 7, an alkoxy group having a carbon atom number of 1 to 7, or an alkenyl group having a carbon atom number of 2 to 7; and it is more preferable that $R^{LC31}$ is an alkyl group having a carbon atom number of 2 or 3, and that $R^{LC32}$ is an alkyl group having a carbon atom number of 2.

The general formula (LC4) can be preferably selected from one kind or two or more kinds of the compounds represented by general formula (LC4-a) to general formula (LC4-c), and the general formula (LC5) can be preferably selected from one kind or two or more kinds of the compounds represented by general formula (LC5-a) and general formula (LC5-c).

[Formula 34]

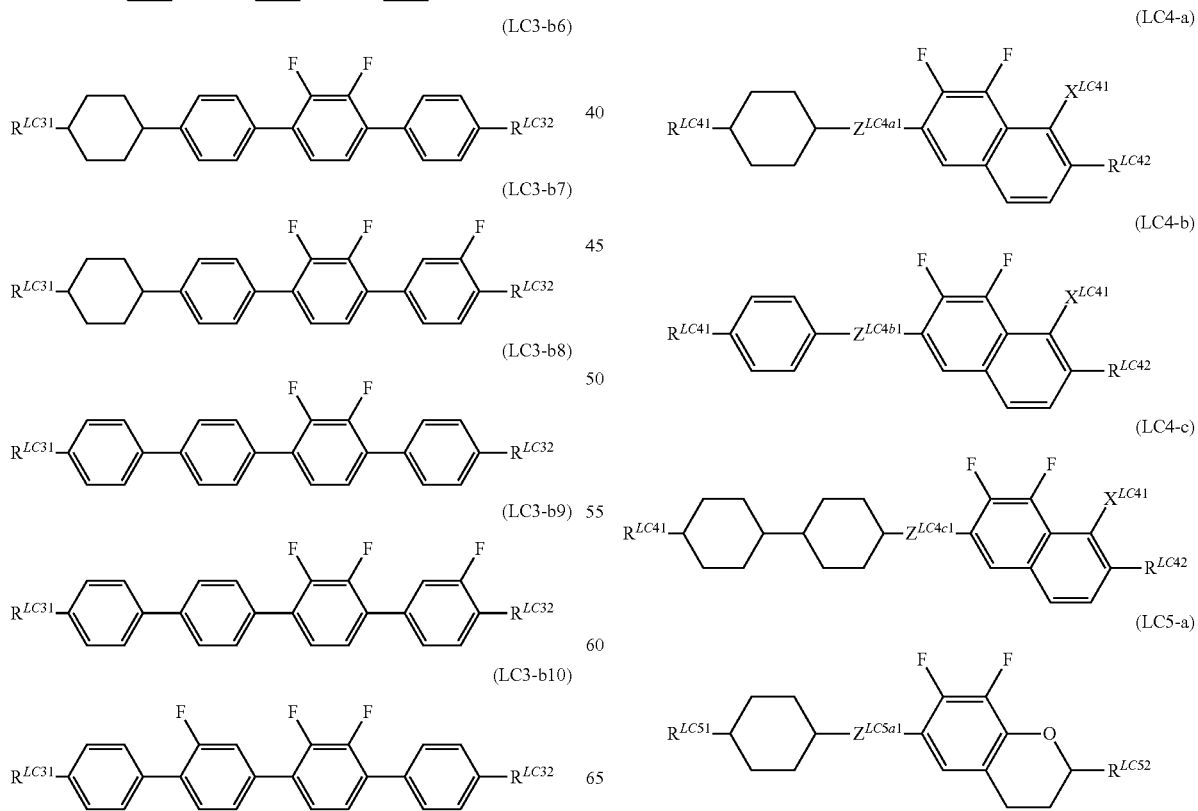

-continued (LC5-b)

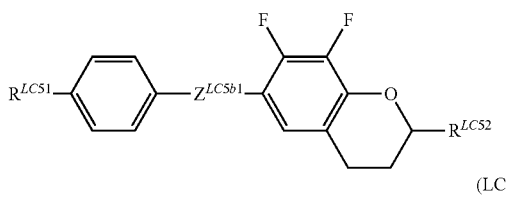

(LC5-c)

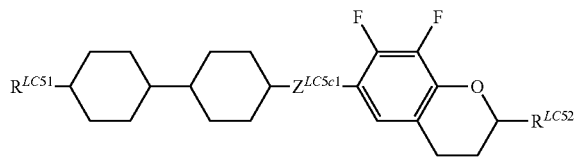

(In the formula, $R^{LC41}$, $R^{LC42}$ and $X^{LC41}$ each independently represent the same meanings as those of $R^{LC41}$ $R^{LC42}$ and $X^{LC41}$ of the general formula (LC4); $R^{LC51}$ and $R^{LC52}$ each independently represent the same meanings as those of $R^{LC51}$ and $R^{LC52}$ of the general formula (LC5); and $Z^{LC4a1}$, $Z^{LC4b1}$, $Z^{LC4c1}$, $Z^{LC5a1}$, $Z^{LC5b1}$ and $Z^{LC5c1}$ each independently represent a single bond, —CH═CH—, —C≡C—, —CH$_2$CH$_2$—, —(CH$_2$)$_4$—, —COO—, —OCH$_2$—, —CH$_2$O—, —OCF$_2$— or —CF$_2$O—.)

It is preferable that $R^{LC41}$, $R^{LC42}$, $R^{LC51}$ and $R^{LC52}$ are each independently an alkyl group having a carbon atom number of 1 to 7, an alkoxy group having a carbon atom number of 1 to 7, an alkenyl group having a carbon atom number of 2 to 7, or an alkenyloxy group having a carbon atom number of 2 to 7.

It is preferable that $Z^{LC4a1}$ to $Z^{LC5c1}$ each independently represent a single bond, —CH$_2$O—, —COO—, —OCO—, —CH$_2$CH$_2$—; and it is more preferable that they represent a single bond.

The fourth component is so-called a non-polar liquid crystal compound whose dielectric anisotropy is around 0, and can be exemplified as the compounds represented by general formula (LC6).

[Formula 35]

(LC6)

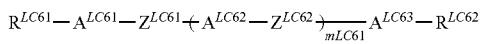

(in the formula, $R^{LC61}$ and $R^{LC62}$ each independently represent an alkyl group having a carbon atom number of 1 to 15, in which one or two or more of the CH$_2$ groups in the alkyl group can be substituted with —O—, —CH═CH—, —CO—, —OCO—, —COO— or —C≡C— without being directly adjacent to an oxygen atom, and one or two or more hydrogen atoms in the alkyl group can be optionally substituted with a halogen; $A^{LC61}$ to $A^{LC63}$ each independently represent one of the structure below.

[Formula 36]

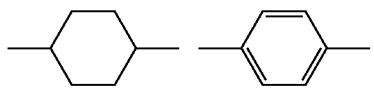

-continued

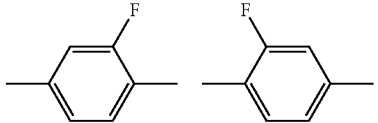

(one or two or more of the —CH$_2$CH$_2$— groups in the cyclohexylene group in the structure can be substituted with —CH═CH—, —CF$_2$O—, —OCF$_2$—; one or two or more of the —CH— groups in the 1,4-phenylene group can be replaced with a nitrogen atom; and $Z^{LC61}$ and $Z^{LC62}$ each independently represent a single bond, —CH═CH—, —C≡C—, —CH$_2$CH$_2$—, —(CH$_2$)$_4$—, —COO—, —OCH$_2$—, —CH$_2$O—, —OCF$_2$— or —CF$_2$O—; $m^{iii1}$ represents 0 to 3. Note that the compound represented by general formula (LC1) to general formula (LC6), and general formula (1) are excluded therefrom.)

It is preferable that $R^{LC61}$ and $R^{LC62}$ are each independently an alkyl group having a carbon atom number of 1 to 7, an alkoxy group having a carbon atom number of 1 to 7, or an alkenyl group having a carbon atom number of 2 to 7; and it is most preferable that the alkenyl group has one of the structures below.

[Formula 37]

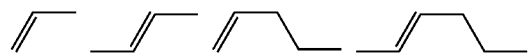

(the right side end of the structure in the formula above shall be combined to the ring structure.)

It is preferable that $A^{LC61}$ to $A^{LC63}$ each independently have one of the structures below.

[Formula 38]

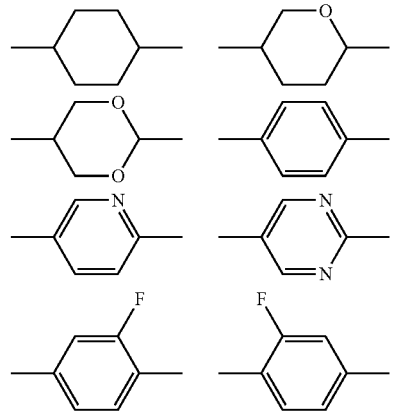

It is preferable that $Z^{LC61}$ and $Z^{LC62}$ each independently represents a single bond, —CH$_2$CH$_2$—, —COO—, —OCH$_2$—, —CH$_2$O—, —OCF$_2$— or —CF$_2$O—.

The general formula (LC6) can be preferably selected from one kind or two or more kinds of the compounds represented by general formula (LC6-a) to general formula (LC6-m).

[Formula 39]

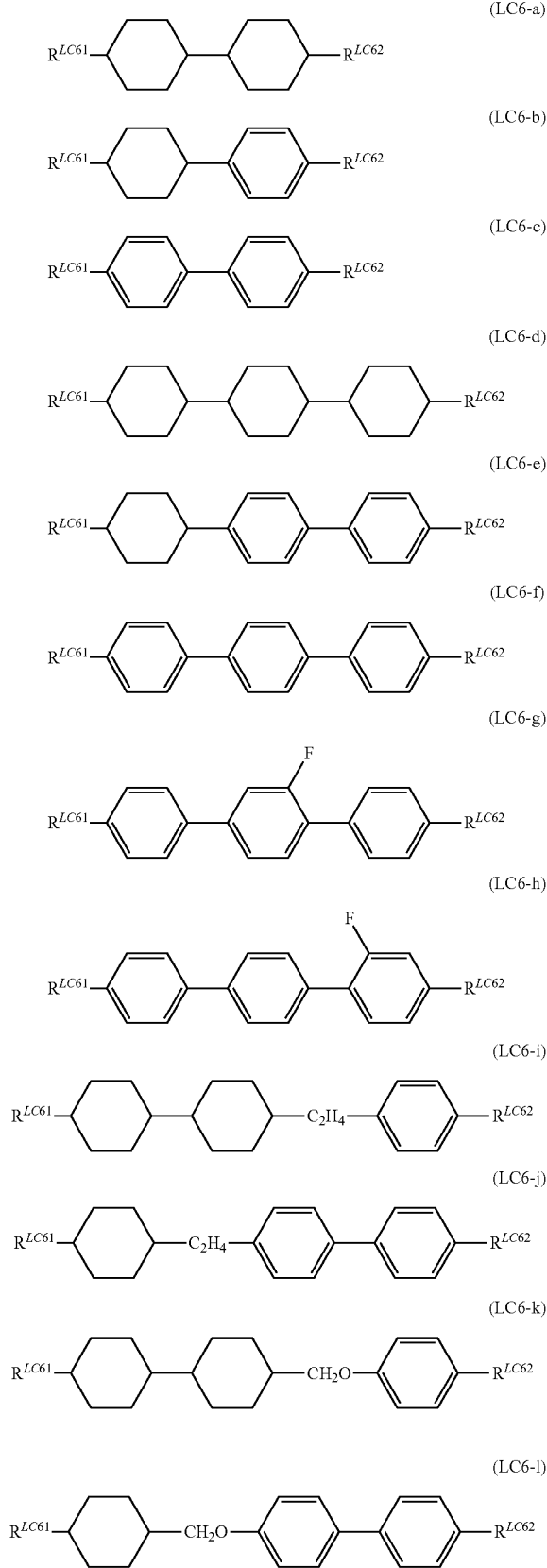

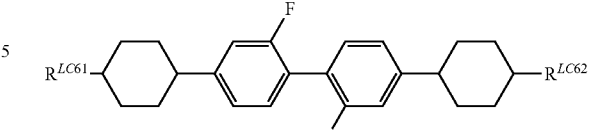

(In the formula, it is preferable that $R^{LC61}$ and $R^{LC62}$ are each independently an alkyl group having a carbon atom number of 1 to 7, an alkoxy group having a carbon atom number of 1 to 7, an alkenyl group having a carbon atom number of 2 to 7, or an alkenyloxy group having a carbon atom number of 2 to 7.)

In the present invention, the compound represented by general formula (1) can be produced as follows. The essences and the scope of the present invention, of course, are not bound by these production examples.

(Manufacturing Method 1)

The compound represented by general formula (2),

[Formula 40]

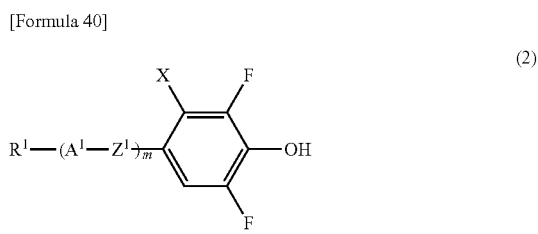

(2)

(In the formula, $R^1$, $A^1$, $Z^1$, X and m each independently represent the same meanings as those of $A^1$, $Z^1$, $R^1$, X and m of general formula (1).), was made into a phenolate by using a base, which was then reacted with the compound represented by general formula (3),

[Formula 41]

$$X^1-R^2 \qquad (3)$$

(in the formula $R^2$ represents the same meaning as that of $R^2$ of general formula (1); $X^1$ represents chlorine, bromine, iodine, benzenesulfonyloxy group, p-toluenesulfonyloxy group, methanesulfonyloxy group or trifluoromethanesulfonyloxy group.), so as to prepare the compound represented by general formula (1).

The base to be used here can be preferably include metal hydrides, metal carbonates, metal phosphates, metal hydroxides, metal carboxylates, metal amides and metals. In particular, alkali metal hydrides, alkali metal phosphates, alkali metal phosphates, alkali metal carbonates, alkali metal hydroxides, alkali metal amides and alkali metals are preferably exemplified. Furthermore, alkali metal phosphates, alkali metal hydrides and the alkali metal carbonates are more preferably exemplified. It is each preferable that the alkali metal hydrides can include lithium hydride, sodium hydride and potassium hydride; that the alkali metal phosphates can include tripotassium phosphate; and that the alkali metal carbonates can include sodium carbonate, sodium hydrogen carbonate, cesium carbonate, potassium carbonate and potassium hydrogen carbonate.

Any reaction solvent can be used so long as the reaction can progress, but it is preferable to use ether type solvents, chlorine type solvents, hydrocarbon type solvents, aromatic type solvents and polar solvents. It is each preferable that the ether type solvents can include 1,4-dioxane, 1,3-dioxane, tetrahydrofuran, diethyl ether and t-butyl methyl ether; that the chlorine type solvents can include dichloromethane, 1,2-dichloroethane and carbon tetrachloride; that the hydrocarbon type solvents can include pentane, hexane, cyclohexane, heptane and octane; that the aromatic type solvents can include benzene, toluene, xylene, mesitylene, chlorobenzene and dichlorobenzene; and that the polar solvent can include N,N-dimethylformamide, N-methylpyrrolidon, dimethyl sulfoxide and sulfolane. In particular, an ether type solvent such as tetrahydrofuran and diethyl ether, and a polar solvent such as N,N-dimethylformamide are more preferable. Also, each solvent can be used alone, or used as a mixture of two or more kinds thereof.

The reaction temperature can be from the freezing point of a solvent to the reflux temperature range thereof, but it is preferably from 0° C. to 150° C., and more preferably from 30° C.' to 120° C. In addition, after producing the phenolate, it can be isolated before it is reacted with the compound represented by general formula (3). Or, it can be reacted without isolation. However, it is favorable that it can be reacted without isolation due to the complexity of the handling.

(Manufacturing Method 2)

The compound represented by the general formula (2) is reacted with the compound represented by general formula (4) in the presence of an azodicarboxylic acid diester and a phosphine,

[Formula 42]

HO—R²               (4)

(In the formula R² represents the same meaning as that of R² of general formula (1).), so as to obtain the compound represented by general formula (1).

Any solvent can be used so long as the reaction can be favorably progressed, but it is preferable to use an ether type solvent such as THF, diethyl ether, diisopropyl ether, an aromatic type solvent such as benzene, toluene and xylene, a halogen type solvent such as dichloromethane, chloroform and carbon tetrachloride. In particular, it is more preferable to use THF or toluene.

Any reaction temperature can be selected as long as the reaction can be favorably progressed, but it can be preferably from −30° C. to 40° C., and more preferably from −20° C. to 20° C., and yet more preferably from −20° C. to an ice cooling temperature.

Any azodicarboxylic acid ester can be used as long as the reaction can be favorably progressed, but it is preferable to use diethyl azodicarboxylate or diisopropyl azodicarboxylate.

The phosphine to be used is preferably triphenylphosphine.

(Manufacturing Method 3)

The compound represented by general formula (7-1) is as follows.

[Formula 43]

R¹-(A¹-Z¹)ₙ-A²-X²               (7-1)

(In the formula, R¹, A¹ and Z¹ each independently represent the same meaning as those of R¹, A¹ and Z¹ of general formula (1);

A² is selected from the group consisting of:

(b) 1,4-phenylene group (in which in the group, one —CH═ group or noncontiguous two or more —CH═ groups can be replaced with a group of —N═, and in which in the group the hydrogen atom can be replaced with a fluorine atom.), and (C) naphthalene-2,6-diyl group (in which in the group, one —CH═ group or noncontiguous two or more —CH═ groups can be replaced with a group of —N═, and in which in the group, the hydrogen atom can be replaced with a fluorine atom.); and X² represents general formula (B-1) or (B-2);

[Formula 44]

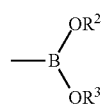
(B-1)

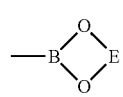
(B-2)

(In the formula, R² and R³ each independently represent a straight or branched alkyl group having a carbon number of 1 to 5, or a hydrogen atom; E represents —(CH₂)ₛ— in which one or more hydrogen atoms existing in the group can be each independently substituted with a methyl group; and s represents 2. 3 or 4.);

n represents 0 to 3 in which when n is 2 or 3 and plural A¹ groups exist, said plural A¹ groups can be the same as or different from each other; and when n is 2 or 3, and plural Z¹ group exist, said plural Z¹ groups can be the same as or different from each other.). The compound above is reacted with the compound represented by general formula (8-1) in the presence of a transition metal catalyst.

[Formula 45]

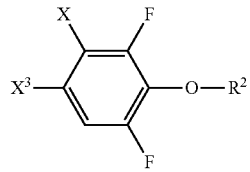
(8-1)

(In the formula R² and X each independently represent the same meaning as those of R² and X of the general formula (1); and X³ represents a group selected from the group consisting of chlorine atom, bromine atom, iodine atom or trifluoromethanesulfonyloxy group.).

Thereby, the compound represented by general formula (9) is obtained.

[Formula 46]

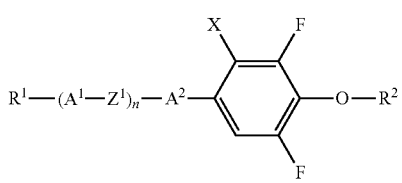

(9)

(In the formula R$^1$, R$^2$ and X each independently represent the same meanings as those of R$^1$, R$^2$ and X of the general formula (1); and A$^2$ represents the same meanings as those of A$^2$ of the general formula (7)).

Any solvent can be used as long as the reaction can be favorably progressed, but it is preferable to use an ether type solvent such as THF, diethyl ether and diisopropyl ether; an aromatic type solvent such as benzene, toluene and xylene; and an amide type solvent such as DMF, N,N-dimethylacetamide and N-methylpyrrolidon. It is more preferable to use THF, DMF or toluene. These solvents can be used alone or a mixture thereof, depending on the necessity. Furthermore, water can be added in order to progress the reaction.

Any reaction temperature can be selected as long as the reaction can be favorably progressed, but it is preferable that the temperature is between room temperature to the reflux temperature of a solvent, and more preferably from 40° C. to the reflux temperature of the solvent.

Any transition metal catalyst can be used as long as the reaction can be favorably progressed, but it is preferable to use a palladium-based transition metal catalyst or a nickel-based transition metal catalyst such as tetrakis(triphenylphosphine)palladium(0), palladium(II) acetate, bis(triphenylphosphine)palladium(II) dichloride, [1,1'-bis(diphenylphosphino)ferrocene]palladium(II) dichloride, and bis[di-tert-butyl(4-dimethylaminophenyl)phosphine]palladium(II) dichloride. It is more preferable to use tetrakis(triphenylphosphine)palladium(0), palladium(I) acetate, bis[di-tert-butyl(4-dimethylaminophenyl)phosphine]palladium(II) dichloride, or [1,1'-bis(diphenylphosphino)ferrocene]palladium(I) dichloride. Also, a phosphine-based ligand can be added in order to progress the reaction.

(Manufacturing Method 4)
The compound represented by general formula (7-2) is as follows.

[Formula 47]

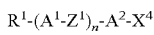 (7-2)

(In the formula, R$^1$, A$^1$ and Z$^1$ each independently represent the same meaning as those of R$^1$, A$^1$ and Z$^1$ of general formula (1);
A$^3$ is selected from the group consisting of:
(b) 1,4-phenylene group (in which in the group, one —CH= group or noncontiguous two or more —CH= groups can be replaced with a group of —N=, and in which in the group the hydrogen atom can be replaced with a fluorine atom.), and
(C) naphthalene-2,6-diyl group (in which in the group, one —CH= group or noncontiguous two or more —CH= groups can be replaced with a group of —N=, and in which in the group, the hydrogen atom can be replaced with a fluorine atom.);
X$^4$ represents a group selected from the group consisting of chlorine atom, bromine atom, iodine atom or trifluoromethanesulfonyloxy group.);

n represents 0 to 3 in which when n is 2 or 3 and plural A$^1$ groups exist, said plural A$^1$ groups can be the same as or different from each other; and when n is 2 or 3, and plural Z$^1$ group exist, said plural Z$^1$ groups can be the same as or different from each other.).

The compound above is, in the presence of a transition metal catalyst, reacted with the compound represented by general formula (8-2).

[Formula 48]

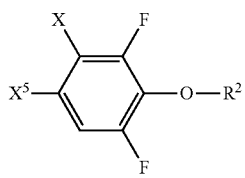

(8-2)

(In the formula, R$^2$ and X each independently represent the same meaning as those of R$^2$ and X of the general formula (1); and X$^5$ represents general formula (B-1) or (B-2);

[Formula 49]

(In the formula, R$^2$ and R$^3$ each independently represent a straight or branched alkyl group having a carbon number of 1 to 5, or a hydrogen atom; E represents —(CH$_2$)$_s$— in which one or more hydrogen atoms existing in the group can be each independently substituted with a methyl group; and s represents 2, 3 or 4.).

The compound represented by general formula (9) is as follow.

[Formula 50]

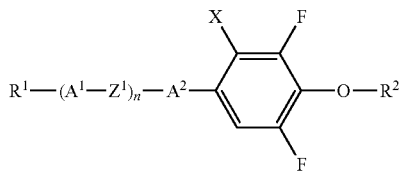

(9)

(In the formula R$^1$, R$^2$ and X each independently represent the same meanings as those of R$^1$, R$^2$ and X of the general formula (1); and A$^2$ represents the same meanings as that of A$^2$ of the general formula (7)).

Thereby the compound represented by the general formula (9) can be obtained.

The conditions such as the solvent to be used, the reaction temperature, and the transition metal catalyst to be use are the same as the conditions described for the manufacturing method 3.

The liquid crystal display element using the liquid crystal composition containing the compound of the present invention can be useful since it satisfies both requirements of the fast response and the suppressed display defects, and particularly it is useful for a liquid crystal display device to drive an active matrix. Therefore, it can be applicable to a liquid crystal display element of VA mode, PSVA mode, PSA mode, IPS mode or ECB mode.

Next, a favorable embodiment of the liquid crystal display element of the present invention is described with reference to the drawings.

FIG. 1 is a cross-sectional view of a liquid crystal display element including two substrates opposed to each other, a sealing material disposed between the substrates, and liquid crystal confined in the sealed region surrounded by the sealing material.

In details, FIG. 1 illustrates an embodiment of a liquid crystal display element which includes a back plane in which a substrate (a) 100 is provided with TFT layers 102 and pixel electrodes 103 formed thereon, onto which a passivation film 104 and an alignment film (a) 105 are provided; a front plane opposed to the back plane, the front plane including a substrate (b) 200 which is provided with a black matrix 202, a color filter 203, a planarized film (overcoat layer) 201, and transparent electrode 204, onto which an alignment layer (b) 205 is provided; a sealing material 301 disposed between the substrates; and a liquid crystal layer 303 confined in a sealed region surrounded by the sealing material, in which the substrate surface contacting the sealing material 301 is provided with protrusions 304.

So long as the substrate (a) or the substrate (b) is made of substantially transparent material, there is no specific limitation, and it can be of glass, ceramic materials, and resin materials. The resin substrate can include cellulose and cellulose derivative such as triacetylcellulose and diacetylcellulose; polycycloolefin derivative, polyester such as polyethylene terephthalate and polyethylenenaphthalate; polyolefin such as polypropylene and polyethylene; polycarbonate, polyvinyl alcohol, polyvinyl chloride, polyvinylidene chloride, polyamide, polyimide, polyimide amide, polystyrene, polyacrylate, polymethylmethacrylate, polyethersulfone, and polyarylate, and furthermore, inorganic organic composite material such as fiberglass-epoxy resin and fiberglass-acrylic resin.

In the case where a resin substrate is used, a barrier film is preferably provided. The barrier film serves to reduce the moisture permeability of the resin substrate, thereby improving the reliability of the electric properties of the liquid crystal display element. The barrier film is not particularly limited and can be made of any material which has a high transparency and a low water vapor permeability. Generally, it can be a thin film formed from an inorganic material such as silicon oxide by means of vapor deposition, sputtering, or a chemical vapor deposition method (CVD method).

In the present invention, the substrate (a) and the substrate (b) can be made of the same material as, or different material from each other, and there is no specific limitation. A glass substrate can be preferably used since a liquid crystal display element with excellent thermal resistance and dimensional stability can be produced. Alternately, a resin substrate can be preferably used since it is suitable for a manufacturing method through a roll-to-roll process, and can appropriately accomplish the improvements of light weight and flexibility. Also, if focusing on imparting flatness and thermal resistance, a combination of a resin substrate and a glass substrate can bring good results.

In the back plane, the substrate (a) 100 is provided with TFT layers 102 and pixel electrodes 103 thereon. These components are formed through an array process which is generally used. Onto this, the passivation film 104 and the alignment film (a) 105 are formed to obtain the back plane.

The passivation film 104 (which is also called as an inorganic protective film) is a film to protect the TFT layers. Generally, it is a nitride film (SiNx), an oxide film (SiOx) and etc. formed by means of a chemical vapor deposition (CVD) technique.

In addition, the alignment film (a) 105 is a film having a function to align a liquid crystal, and generally, a polymer material such as polyimide can be often used. An alignment agent solution including a polymer material and a solvent can be used as a coating solution. Since the alignment film might inhibit the adhesive force with the sealing material, it can be thus subject to a pattern application within a sealed region. The application can be performed by using a printing method such as flexographic printing method, or a droplet discharge method such as ink jet. The alignment agent solution as applied can be crosslinked and cured by baking after the solvent is evaporated by preliminary drying it. Then, an alignment treatment can be performed in order to exhibit the an alignment function.

The alignment treatment can be generally performed by a rubbing method. The polymer film formed as described above is rubbed against one direction with a rubbing cloth made of fibers of rayon or the like, thereby giving it the ability of liquid crystal alignment.

Also, an optical alignment method can be used. The optical alignment method is a method to produce the alignment ability by irradiating an alignment film containing an organic material having a photosensitivity with polarized lights, and therefore, it does not cause scratches or dusts on the substrate unlike the rubbing method. An example of such an organic material useful in the optical alignment method is a material containing a dichroic dye. As a dichroic dye to be used, there can be a dichroic dye which has a group to induce the molecular alignment by means of Weigert effect based on the dichroism as an origin of the alignment ability of the liquid crystal (the group is hereinafter abbreviated as an "optical alignment group."), such as isomerization reaction (e.g., azobenzene group), dimerization reaction (e.g., cinnamoyl group), optical crosslinking reaction (e.g., benzophenone group), or optical decomposition reaction (e.g., polyimide group). The coated alignment agent solution is preliminarily dried to evaporate the solvent, followed by irradiation with lights having a certain polarization (polarized light), thereby giving the alignment film an alignment ability in any direction.

On the other hand, the front plane includes, on the substrate (b) 200, the black matrix 202, the color filter 203, the planarized film 201, the transparent electrode 204, and the alignment film (b) 205.

The black matrix 202 is formed by, for example, a pigment dispersion method. In details, on the substrate (b) 200 having provided the barrier film 201, there is applied a color resin liquid in which a black colorant has been uniformly dispersed for the purpose of forming the black matrix, thereby forming a colored layer. Then, the colored layer is cured by baking. Thereon, a photoresist is coated and then preliminarily baked. The photoresist is exposed to lights through a mask pattern, and then, developed to make pattern the colored layer. Then, the photoresist layer is removed, and the colored layer is baked to complete the formation of the black matrix 202.

Alternatively, a photoresist type pigment dispersion liquid can be used. In this case, a photoresist type pigment dispersion liquid is applied and preliminarily baked, which is followed by exposure to lights through a mask pattern, and then developed to pattern the colored layer. Then, the photoresist layer is removed, and the colored layer is baked to complete the formation of the black matrix 202.

The color filter 203 is formed by means of a pigment dispersion method, an electrodeposition method, a printing method, or a staining method. In the pigment dispersion method, for example, a color resin solution in which a pigment (e.g., red) has been uniformly dispersed is applied onto the substrate (b) 200 and then cured by baking, onto which a photoresist is applied and preliminarily baked. The photoresist is exposed with lights through a mask pattern, then developed to accomplish the patterning. Then, the photoresist layer is removed, and it is baked again, thereby completing the formation of a (red) color filter 203. The color filters can be formed in any order with respect to the colors. In the same manner, a green color filter 203 and a blue color filter 203 are formed.

The transparent electrode 204 is formed on the color filter 203 (if necessary, the overcoat layer (201) is optionally formed on the color filter 203 to flatten a surface). The transparent electrode 204 preferably has a higher light transmittance and a lower electric resistance. The transparent electrode 204 is formed by means of sputtering an oxide film such as ITO.

Also, for the purpose to protect the transparent electrode 204, a passivation film can be formed on the transparent electrode 204 in some cases.

The alignment film (b) 205 is the same as the alignment film (a) 105 as mentioned above.

As explained above, while the details of the specific embodiment of the back plane and front plane used in the present invention was described, the present invention is not limited to the specific embodiment. The changes to the embodiment depending on a desired liquid crystal display element can be optionally made.

The shape of the columnar spacer is not limited, and can have any shape. In particular, its horizontal cross section can be provided with any shape such as a circular, a rectangular or a polygonal shape. However, its horizontal cross section preferably has a shape of a circular or a regular polygonal shape in view of margin for misalignment in the production process. Also, the protrusions preferably have a shape of truncated cone or truncated pyramid.

The material of the columnar spacer is not specifically limited, so long as it is insoluble in the sealing material, an organic solvent used in the sealing material, or the liquid crystal. In particular in view of processability and light weight it can be preferably a synthetic resin (curable resin). By the way, the protrusion can be provided on a surface of the first substrate where it contacts the sealing material by means of a photolithography method or a droplet ejection method. For such reasons, a photocurable resin suitable for the photolithography method and the droplet ejection method can be preferably used.

As an example, an explanation is made in a case where the columnar spacers are formed by means of a photolithography method.

A resin solution (which does not contain a colorant) used for forming the columnar spacer is coated on the transparent electrode 204 of the front plane. Then, this resin layer is cured by baking. There, a photoresist is coated and then preliminarily baked. The photoresist is exposed with lights through a mask pattern, and then developed to obtain a patterning of the resin layer. Then, the photo resist layer is removed, and then, the resin layer is baked to finish the formation of the columnar spacer.

The position to form the columnar spacers can be determined as needed by using a mask pattern. Therefore, both the inside of the sealed region of the liquid crystal display element and the outside thereof (the part where the sealing material is applied) can be simultaneously formed. Also, it is preferable that the columnar spacers are formed above the black matrix to avoid the deterioration of the quality of the sealed region. The columnar spacers formed through the photolithography method as explained above can be sometimes called as a column spacer or a photo spacer.

The material of the spacer to be used can be a mixture containing, for example, a negative type water-soluble resin, such as a PVA-stilbazo photosensitive resin, a polyfunctional acrylic monomer, an acrylic acid copolymer, and a triazole-based initiator. Alternatively, there can be a method using a color rein, in which a colorant has been dispersed in a polyimide resin. There is no specific limitation in the present invention, and the spacer can be prepared by using known materials suitable for the liquid crystal and the sealing material.

In this way, the columnar spacers are formed on the surface of the front plane where it becomes a sealed region, before the sealing material (represented by the symbol 301 in FIG. 1) is coated on the surface of the back plane where the seal material contacts.

The material of the sealing material is not particularly limited. A curable resin composition can be used which is prepared by adding a polymerization initiator to an epoxy-based or acrylic-based photocurable resin, thermosetting resin, or optically and thermally curable resin. Also, fillers made of an inorganic or organic material can be added in some cases to adjust moisture permeability, elastic modulus, and viscosity. Such fillers may have any shape such as spherical shape, fibrous shape, or amorphous shape. Furthermore, a spherical or fibrous gap material having a single dispersion diameter can be mixed to favorably control the cell gap, and a fibrous material which can be easily entangled around the protrusion formed above the substrate can be mixed to enhance the adhesion to the plates. It is desirable that the diameter of the fibrous material used in this case is less than around $1/5$ to $1/10$ of the cell gap, and the length of the fibrous material is preferably shorter than the coating width of the sealing material.

The material of the fibrous material is not particularly limited so long as a predetermined shape can be obtained. It can be appropriately selected from synthetic fibers such as cellulose, polyamide, and polyester, and inorganic materials such as glass and carbon.

Regarding the method for coating the sealing material, it can be coated by means of a printing method or a dispensing method, but a dispensing method is prefer because of using a small amount of the sealing material. The position to coat the sealing material is set above the position of the black matrix in order to avoid adversely affecting the sealed region. In order to form a liquid crystal dropped region in the subsequent process (to prevent the liquid crystal from leaking), the shape of the sealing material is a closed loop.

A liquid crystal is dropped at the closed loop structure (sealed region) of the front plane, the closed loop structure having been formed by application of the sealing material. In general a disperser is used. Since the amount of the liquid crystal to be dropped should be equivalent to the capacity of the liquid crystal cell, the amount is basically equal to the volume that is the product of the height of the columnar spacer and the coated area of the sealing material. However, in order to reduce the leakage of the liquid crystal during the cell bonding process or optimize the display characteristics, the amount of the liquid crystal to be dropped can be appropriately adjusted, or the positions to which the liquid crystal are dropped can be dispersed.

Then, the back plane is bonded to the front plane in which the sealing material has been coated and the liquid crystal has been dropped. In details, the front plane and the back plane are attached to a stage having a mechanism for holding a substrate, such as an electrostatic chuck, and then the front plane and the back plane are disposed at a position (in a distance) such that the alignment film (b) of the front plane is opposed to the alignment film (a) of the back plane while the sealing material does not contact the other substrate. In this state, a pressure inside the system is reduced. After the completion of the pressure reduction, the positions of the front plane and back plane are adjusted while the bonding parts of the front plane and the back plane are being checked (alignment process). After the bonding parts are adjusted, the substrates are moved close to each other to a position at which the sealing material on the front plane contacts the backplane. In this state, the inside of the system is filled with an inert gas, and the vacuum is gradually reduced and returned to the normal pressure. In this process, atmospheric pressure enables the front plane and the back plane to be bonded to each other, so as to create a cell gap with the height of the columnar spacers. In this state, the sealing material is irradiated with ultraviolet lights to cure the sealing material, thereby forming the liquid crystal cell. Then, a heating process is optionally carried out to promote the curing of the sealing material. The heating process is often carried out in order to enhance the adhesion of the sealing material and the reliability of the electric properties.

EXAMPLES

Hereinafter, the present invention is explained more in detail with reference to the Examples, but the construction of the present invention shall not be limited to the Examples. The term "%" in the Examples and the Comparative Examples below means "mass %." The specific resistivity value of a liquid crystal composition was obtained by injecting a liquid crystal composition into a measurement cell, to which a voltage of 1V (DC) was applied at a temperature of 25° C. for measurement. The measurement of a phase transition temperature was carried out by using both a polarizing microscope provided with a temperature control stage and a differential scanning calorimeter (DSC).

$T_{n-i}$ represents a nematic-isotropic phase transition temperature.

The compounds used are abbreviated as follows.
DMF: N,N-dimethylformamide;
Me: Methyl group; and
Pr: n-propyl group.

Example 1

The Production of 2,3,6-trifluoro-4-[4-(4-propylphenyl)phenyl]-1-allyloxybenzene (1b-11)

[Formula 51]

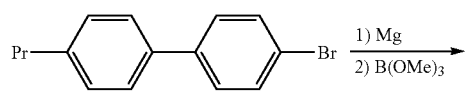

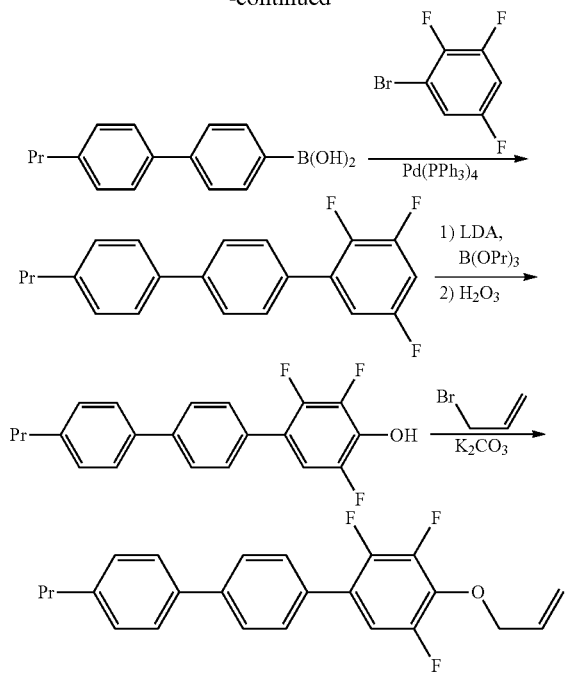

(1-1)
In a dry nitrogen atmosphere, metal magnesium (2.6 g) was suspended in THF (10 mL), into which a solution of 4-(4-propylphenyl)bromobenzene (25 g) having dissolved in THF (100 mL) was gradually added at a speed to allow reflux in the system, followed by continuing stirring at room temperature for one hour. Then, under ice cooling, triisopropyl borate (10.4 g) was slowly added, followed by stirring at room temperature for 30 minutes. The system was cooled with ice again, and 10° % hydrochloric acid (100 mL) was slowly added for liquid separation, and THF (100 mL) was added to the aqueous layer for extraction. The organic layer merged was washed with a saturated sodium chloride aqueous solution (100 mL) twice, into which anhydrous sodium sulfate was added and dried. By distilled away the organic solvent under reduced pressure, a crude product of 4-(4-propylphenyl)phenylborate (26.6 g) was obtained.

(1-2)
In a dry nitrogen atmosphere, the crude product of 4-(4-propylphenyl)phenylborate (26.6 g) produced in step (1-1), 2,3,5-trifluorobromobenzene (19.2 g), potassium carbonate (18.8 g), tetrakis(triphenylphosphine)palladium (0) (2.10 g) and ethanol (200 mL) were mixed, and then, the stirring was continued for 15 hours at a temperature to allow reflux of the solvent. After cooling it to room temperature, the crystals as precipitated were filtered, which were then dried under a reduced pressure, dissolved in a mixture solvent (toluene/hexane=2:1; 150 mL), and purified through a silica gel column chromatography. After the solvent was distilled away under reduced pressure, recrystallization in a mixture solvent of toluene and hexane was carried out to obtain 2,3,5-trifluoro-1-[4-(4-propylphenyl)phenyl]benzene (18.0 g).

(1-3)
In a dry nitrogen atmosphere, diisopropylamine (7.3 g) and THF (180 mL) were mixed and cooled at −40° C., into which 1.6 mol/L n-butyllithium hexane solution (40 mL) was gradually added, and stirring was further carriout out at −40° C. for one hour. Then, a solution having dissolved 2,3,5-trifluoro-1-[4-(4-propylphenyl)phenyl]benzene (18.0 g) produced in the step (1-2) and triisoproyl borate (13.5 g) in THF (40 mL) was added gradually, and stirring was further carried out at −40° C. for one hour. After the temperature was gradually raised to room temperature, they were cooled with ice, into which water (10 mL) was gradually added and 10% hydrochloric acid (60 mL) was gradually added for liquid separation. After the organic layer was washed with water (50 mL), 30% hydrogen peroxide water (8.1 g) was gradually added, and stirring was continued for 40 hours at 50° C. Cooling with ice, 10% sulfite sodium aqueous solution (100 mL) and toluene (100 mL) were added for liquid separation, and the organic layer was washed with 10% sulfite sodium aqueous solution (100 mL) and a saturated sodium chloride aqueous solution (100 mL), into which anhydrous sodium sulfate was added for drying. After the organic solvent was distilled away under reduced pressure, purification was carried out through a silica gel column chromatography to obtain a crude product of 2,3,6-trifluoro-4-[4-(4-propylphenyl)phenyl]phenol (19.0 g).
(1-4)

In a dry nitrogen atmosphere, 2,3,6-trifluoro-4-[4-(4-propylphenyl)phenyl]phenol (19.0 g) produced in the step (1-3), allyl bromide (7.4 g) and anhydrous potassium carbonate (11.5 g) were suspend in DMF (100 mL), and stirred at 40° C. for 4 hours. Cooling to room temperature, toluene (50 mL) was added and insoluble matters were removed by filtration, and then water (100 mL) was added for liquid separation. After the organic layer was washed with water (100 mL) and a saturated sodium chloride aqueous solution (150 mL), anhydrous sodium sulfate was added for drying. After the organic solvent was distilled away under reduced pressure, purification was carried out through a silica gel column chromatography and recrystallization was carried out in a mixture solvent of acetone and ethanol to obtain 2,3,6-trifluoro-4-[4-(4-propylphenyl)phenyl]-1-allyloxybenzene (1b-11).

The phase transition temperature (° C.): Cr 115 SmA 126 N 132 Iso

MS m/z: 382 [M+]

¹HNMR (CDCl₃, TMS internal standard) δ (ppm)=7.67 (2H, d, J=8.3 Hz), 7.57-7.54 (4H, m), 7.28 (2H, d, J=8.0 Hz), 7.04-6.99 (1H, m), 6.13-6.03 (1H, m), 5.42 (1H, dd, J1=1.2 Hz, J2=17.2 Hz), 5.31 (1H, dd, J1=0.9 Hz, J2=10.3 Hz), 4.73 (2H, d, J=6.0 Hz), 2.64 (2H, t, J=7.5 Hz), 1.67 (2H, sex, J=7.4 Hz), 0.98 (3H, t, J=7.3 Hz)

Example 2

Production of 2,6-difluoro-4-[4-(trans-4-propylcyclohexyl)phenyl]-1-allyloxybenzene (1b-1)

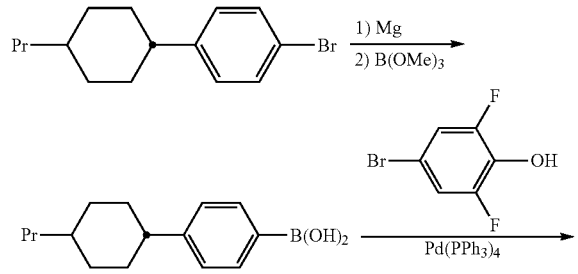

[Formula 52]

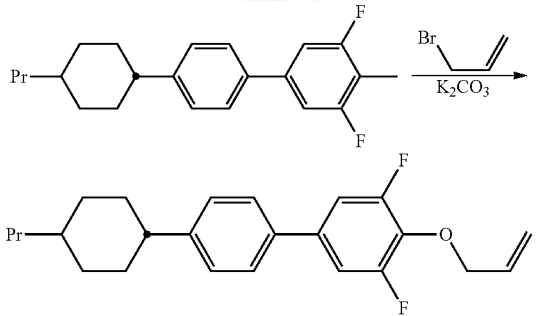

(2-1)

In a dry nitrogen atmosphere, metal magnesium (4.7 g) was suspended in THF (10 mL), into which a solution of 4-(trans-4-propylcyclohexyl)bromobenzene (50.0 g) having dissolved in THF (200 mL) was gradually added at a speed to allow reflux in the system, followed by continuing stirring at room temperature for one hour. Then, under ice cooling, a solution having dissolved trimethyl borate (22.2 g) in THF (40 mL) was slowly added, followed by stirring at room temperature for 2 hours. Cooling with ice again, 10% hydrochloric acid (100 mL) was gradually added for liquid separation. Then, THF (100 mL) and toluene (50 mL) were added to the aqueous layer for extraction, and the organic layer merged was washed with a saturated sodium chloride aqueous solution (100 mL) twice, into which anhydrous sodium sulfate was added for drying. By distilled away the organic solvent under reduced pressure, a crude 4-(trans-4-propylcyclohexyl)phenylborate (46.8 g) was obtained.
(2-2)

4-bromo-2,6-difluorophenol (33.8 g), tetrakis(triphenylphosphine)palladium (0) (5.61 g), ethanol (170 mL) and 2 mol/L potassium carbonate aqueous solution (160 mL) were mixed and heated to a temperature of 60° C. While heating, a solution having dissolved 4-(trans-4-propylcyclohexyl)phenylborate (46.8 g) prepared in step (2-1) in ethanol (150 mL) was gradually dropped. Stirring was further continued at 60° C. for 4 hours. Then, cooling to room temperature, ethyl acetate (200 mL) was added therein for liquid separation. Ethyl acetate (150 mL) was added to the aqueous layer for extraction, and then, the organic layer merged was washed twice with a saturated sodium chloride aqueous solution (200 mL), and sodium sulfate that was diluted was added for drying. The organic solvent was distilled away under reduced pressure, and the residue was purified through a silica gel column chromatography. Then, recrystallization was carried out from hexane to obtain 4-[4-(trans-4-propylcyclohexyl)phenyl]-2,6-difluorophenol (34.9 g).
(2-3)

In a dry nitrogen atmosphere, 4-[4-(trans-4-propylcyclohexyl)phenyl]-2,6-difluorophenol (18.0 g) prepared in step (2-2), allyl bromide (7.3 g), anhydrous potassium carbonate (11.3 g) and DMF (90 mL) were suspend, and stirred at 40° C. for 4 hours. After insoluble matters were removed by filtration, toluene (100 mL) was added for liquid separation. After the organic layer was washed twice with a saturated sodium chloride aqueous solution (100 mL), anhydrous sodium sulfate was added for drying. After the organic solvent was distilled away under reduced pressure, purification was carried out through a silica gel column chromatography. Then, recrystallization was carried out from a mixed solution of acetone and methanol, so as to obtain 2,6-difluoro-4-[4-(trans-4-propylcyclohexyl)phenyl]-1-allyloxybenzene (12.6 g).

The phase transition temperature (° C.): Cr 60 SmA 69 N 129 Iso

MS m/z: 370 [M+]

$^1$HNMR (CDCl$_3$, TMS internal standard) δ (ppm)=7.43 (2H, d, J=7.2 Hz), 7.27 (2H, d, J=7.6 Hz), 7.11 (2H, d, J=8.5 Hz), 6.13-6.03 (1H, m), 5.40 (1H, dt, J1=1.4 Hz, J2=17.2 Hz), 5.28 (1H, d, J=10.2 Hz), 4.67 (2H, d, J=5.8 Hz), 2.53-2.46 (1H, m), 1.92-1.86 (4H, m), 1.52-1.19 (7H, m), 1.11-1.01 (2H, m), 0.91 (3H, t, J=7.2 Hz)

Example 3

Production of 2,6-difluoro-4-[4-(trans-4-propylcyclohexyl]phenyl]-1-(2-buten-1-yloxy)benzene (1b-6)

[Formula 53]

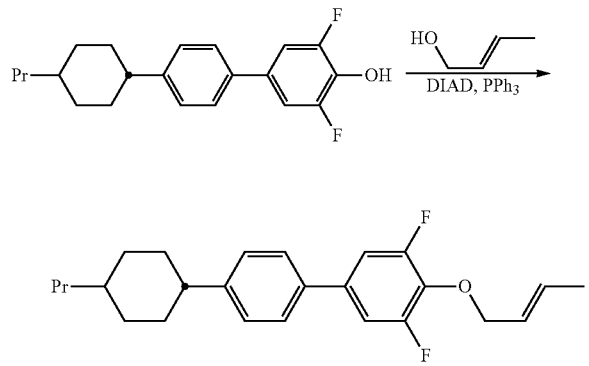

(3-1)

In a dry nitrogen atmosphere, 4-[4-(trans-4-propylcyclohexyl]phenyl]-2,6-difluorophenol (16.9 g) prepared in step (2-2), trans-crotyl alcohol (3.7 g) and triphenylphosphine (14.7 g) were dissolved in THF (85 mL). Cooling with ice, diisopropyl azodicarboxylate (10.9 g) was gradually added. Stirring was further continued at room temperature for 5 hours, and then, water (10 mL) was added. Then, the organic solvent was distilled away under reduced pressure. The residue was dissolved in hexane (200 mL), which was subject to a liquid separation with a mixture solvent of methanol (100 mL) and water (50 mL). Then, the organic layer was washed with a saturated sodium chloride aqueous solution (100 mL), into which anhydrous sodium sulfate was added for drying. After the organic solvent was distilled away under reduced pressure, and the residue was purified through a silica gel column chromatography. Then, recrystallization was carried out in a mixture solvent of acetone and ethanol so as to obtain 2,6-difluoro-4-[4-(trans-4-propylcyclohexyl]phenyl]-1-(2-buten-1-yloxy)benzene (10.1 g).

The phase transition temperature (° C.): Cr 53 SmA 86 N 131 Iso

MS m/z: 384 [M+]

$^1$HNMR (CDCl$_3$, TMS internal standard) δ (ppm)=7.43 (2H, d, J=7.2 Hz), 7.27 (2H, d, J=8.6 Hz), 7.10 (2H, d, J=8.4 Hz), 5.86-5.71 (2H, m), 4.59 (2H, d, J=6.1 Hz), 2.53-2.47 (1H, m), 1.92-1.86 (4H, m), 1.72 (2H, d, J=5.9 Hz), 1.71-1.66 (1H, m), 1.52-1.19 (7H, m), 1.11-1.01 (2H, m), 0.91 (3H, t, J=7.2 Hz)

Example 4

2,6-difluoro-4-[4-(trans-4-(trans-4-propylcyclohexyl]cyclohexyl)phenyl]-1-allyloxybenzene (1e-1)

[Formula 54]

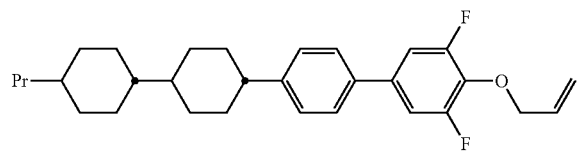

In the same manner as described in the production of Examples 1 to 3, 2,6-difluoro-4-[4-(trans-4-(trans-4-propylcyclohexyl]cyclohexyl)phenyl]-allyloxybenzene was obtained.

MS m/z: 452 [M+]

$^1$HNMR (CDCl$_3$, TMS internal standard) δ (ppm)=7.43 (2H, d, J=7.2 Hz), 7.27 (2H, d, J=7.6 Hz), 7.11 (2H, d, J=8.5 Hz), 6.15-5.95 (1H, m), 5.36 (1H, dd, J1=1.4 Hz, J2=17.1 Hz), 5.24 (1H, dd, J1=1.0 Hz, J2=10.3 Hz), 4.59 (2H, d, J=6.0 Hz), 2.36 (1H, tt, J1=3.1 Hz, J2=12.1 Hz), 1.92-1.66 (8H, m), 1.40-0.78 (15H, m), 0.87 (3H, t, J=7.3 Hz)

Example 5

Production of 2,6-difluoro-4-[2-fluoro-4-(4-propylphenyl)phenyl]-1-allyloxybenzene

[Formula 55]

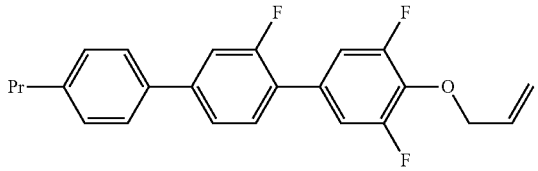

In the same manner as described in the production of Examples 1 to 3, 2,6-difluoro-4-[2-fluoro-4-(4-propylphenyl)phenyl]-1-allyloxybenzene was obtained. The phase transition temperature (° C.): Cr 45 SmA 101 N 110 Iso MS m/z: 382 [M+]

$^1$HNMR (CDCl$_3$, TMS internal standard) δ (ppm)=7.50 (2H, d, J=8.2 Hz), 7.41-7.33 (3H, m), 7.25 (2H, d, J=8.3 Hz), 7.14 (2H, d, J=8.3 Hz), 6.13-6.03 (1H, m), 5.40 (1H, dd, J1=1.4 Hz, J2=17.2 Hz), 5.28 (1H, dd, J1=1.2 Hz, J2=10.3 Hz), 4.69 (2H, d, J=6.0 Hz), 2.63 (2H, t, J=7.5 Hz), 1.67 (1H, sex, J=7.6 Hz), 0.97 (3H, t, J=7.3 Hz)

Example 6

Production of 2,6-difluoro-4-[2-fluoro-4-(4-propyl-phenyl)phenyl]-1-(2-buten-1-yloxy)benzene

[Formula 56]

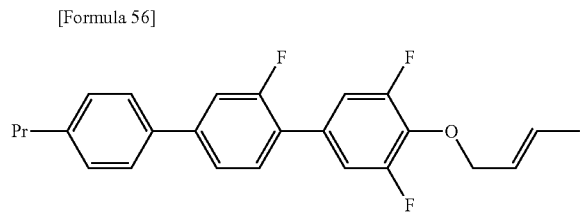

In the same manner as described in the production of Examples 1 to 3, 2,6-difluoro-4-[2-fluoro-4-(4-propylphenyl)phenyl]-1-(2-buten-1-yloxy)benzene was obtained.

The phase transition temperature (° C.): Cr 59 SmA 95 N 111 Iso

MS m/z: 396 [M+]

$^{1}$HNMR (CDCl$_3$, TMS internal standard) δ (ppm)=7.50 (2H, d, J=8.1 Hz), 7.42-7.33 (3H, m), 7.25 (2H, d, J=8.2 Hz), 7.14 (2H, d, J=8.4 Hz), 5.88-5.72 (2H, m), 4.62 (2H, d, J=6.1 Hz), 2.62 (2H, t, J=7.6 Hz), 1.73-1.56 (4H, m), 0.97 (3H, t, J=7.3 Hz)

Comparative Example 1

2,6-difluoro-4-[trans-4-(trans-4-propylcyclohexyl)cyclohexyl]-1-allyloxybenzene

[Formula 57]

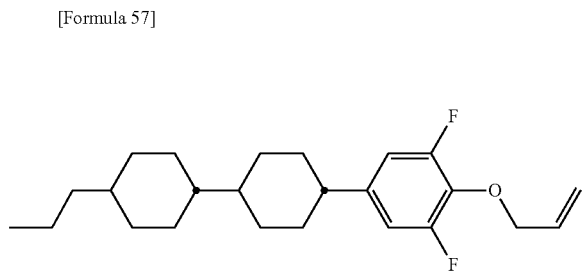

In the same manner as disclosed in an article (Japanese Laid-Open Patent Publication No. 7-258141), 2,6-difluoro-4-[trans-4-(trans-4-propylcyclohexyl)cyclohexyl)cyclohexyl]-1-allyloxybenzene was obtained.

The phase transition temperature (° C.): Cr 30 N 159 Iso

MS m/z: 376 [M+]

$^{1}$HNMR (CDCl$_3$, TMS internal standard) δ (ppm)=6.72 (2H, d, J=9.5 Hz), 6.15-5.95 (1H, m), 5.36 (1H, dd, J1=1.4 Hz, J2=17.1 Hz), 5.24 (1H, dd, J1=1.0 Hz, J2=10.3 Hz), 4.59 (2H, d, J=6.0 Hz), 2.36 (1H, tt, J1=3.1 Hz, J2=12.1 Hz), 1.92-1.66 (8H, m), 1.40-0.78 (15H, m), 0.87 (3H, t, J=7.3 Hz)

Example 7

Preparation of the Liquid Crystal Composition-1

A host liquid crystal composition (H) had a composition below.

[Formula 58]

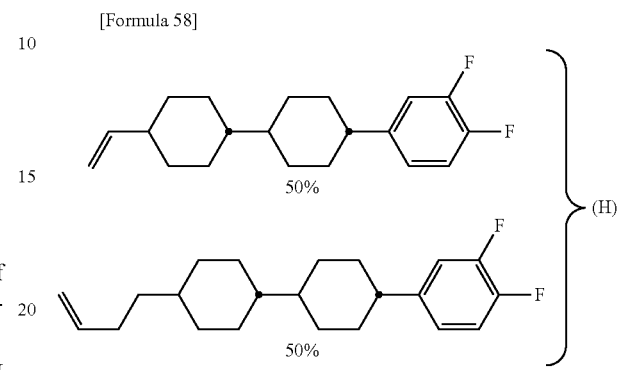

The host liquid crystal composition (H) above was prepared. Here, the physical properties of the composition (H) were as follows.

Nematic phase upper limit temperature (Tn-i): 117.2° C.
Dielectric anisotropy (Δ∈): 4.76
Refractive index anisotropy (Δn): 0.0873
Viscosity (η 20): 20.5 mPa·s Composing 90% of this host liquid crystal (H) and 10% of 2,3,6-trifluoro-4-[4-(4-propylphenyl)phenyl]-1-allyloxybenzene prepared in Example 1, a liquid crystal composition (M-A) was prepared. This composition had the values of an extrapolation $T_{n-i}$, an extrapolation Δ∈, an extrapolation Δn, and extrapolation $η_{20}$ as follows.

Tn-i: 113.9° C.
Δ∈: 0.38
Δn: 0.2524
$η_{20}$: 23.7 mPa·s

It was found that thereby prepared liquid crystal composition (M-A) maintained a uniform nematic liquid crystalline state at room temperature for more than one month. Furthermore, it was found that a liquid crystal display device manufactured by using the liquid crystal composition (M-A) was excellent in the display properties, and that it maintained stable display properties for a long term and showed a high reliability.

Example 8

Preparation of Liquid Crystal Composition-2

Composing 80% of the host liquid crystal (H) and 20% of 2,6-difluoro-4-[4-(trans-4-propylcyclohexyl]phenyl]-1-allyloxybenzene prepared in Example 21, a liquid crystal composition (M-B) was prepared. This composition had the values of an extrapolation $T_{n-i}$, an extrapolation Δ∈, an extrapolation Δn, and extrapolation $η_{20}$ as follows.

$T_{n-i}$: 127.9° C.
Δ∈: 2.86
Δn: 0.1883
η20: 17.7 mPa·s

It was found that thereby prepared liquid crystal composition (M-B) maintained a uniform nematic liquid crystalline state at room temperature for more than one month.

Furthermore, it was found that a liquid crystal display device manufactured by using the liquid crystal composition (M-B) was excellent in the display properties, and that it maintained stable display properties for a long term and showed a high reliability.

Example 9

Preparation of Liquid Crystal Composition-3

Composing 80% of the host liquid crystal (H) and 20% of 2,6-difluoro-4-[4-(trans-4-propylcyclohexyl)phenyl]-1-(2-buten-1-yloxy)benzene prepared in Example 3, a liquid crystal composition (M-C) was prepared. This composition had the values of an extrapolation $T_{n\text{-}i}$, an extrapolation $\Delta\in$, an extrapolation $\Delta n$, and extrapolation $\eta_{20}$ as follows.
$T_{n\text{-}i}$: 127.4° C.
$\Delta\in$: 2.19
$\Delta n$: 0.1926
$\eta_{20}$: 24.9 mPa·s It was found that thereby prepared liquid crystal composition (M-C) maintained a uniform nematic liquid crystalline state at room temperature for more than one month.

Furthermore, it was found that a liquid crystal display device manufactured by using the liquid crystal composition (M-C) was excellent in the display properties, and that it maintained stable display properties for a long term and showed a high reliability.

Example 10

Preparation of Liquid Crystal Composition-4

Composing 80% of the host liquid crystal (H) and 20% of 2,6-difluoro-4-[2-fluoro-4-(4-propylphenyl)phenyl]-1-allyloxybenzene prepared in Example 5, a liquid crystal composition (M-D) was prepared. This composition had the values of an extrapolation $T_{n\text{-}i}$, an extrapolation $\Delta\in$, an extrapolation $\Delta n$, and extrapolation $\eta_{20}$ as follows.
$T_{n\text{-}i}$: 105.7° C.
$\Delta\in$: 5.36
$\Delta n$: 0.2753
$\eta_{20}$: 25.7 mPa·s It was found that thereby prepared liquid crystal composition (M-D) maintained a uniform nematic liquid crystalline state at room temperature for more than one month.

Furthermore, it was found that a liquid crystal display device manufactured by using the liquid crystal composition (M-D) was excellent in the display properties, and that it maintained stable display properties for a long term and showed a high reliability.

Example 11

Preparation of Liquid Crystal Composition-5

Composing 80% of the host liquid crystal (H) and 20% of 2,6-difluoro-4-[2-fluoro-4-(4-propylphenyl)phenyl]-1-(2-buten-1-yloxy)benzene prepared in Example 6, a liquid crystal composition (M-E) was prepared. This composition had the values of an extrapolation $T_{n\text{-}i}$, an extrapolation $\Delta\in$, an extrapolation $\Delta n$, and extrapolation $\eta_{20}$ as follows.
Tn-i: 103.7° C.
$\Delta\in$: 3.76
$\Delta n$: 0.2703
$\eta_{20}$: 27.2 mPa·s It was found that thereby prepared liquid crystal composition (M-E) maintained a uniform nematic liquid crystalline state at room temperature for more than one month.

Furthermore, it was found that a liquid crystal display device manufactured by using the liquid crystal composition (M-E) was excellent in the display properties, and that it maintained stable display properties for a long term and showed a high reliability.

Comparative Example 2

Preparation of Liquid Crystal Composition-4

Composing 80% of the host liquid crystal (H) and 20% of compounds (6) prepared in Comparative Example 1, a liquid crystal composition (M-F) was prepared. This composition had the values of an extrapolation $T_{n\text{-}i}$, an extrapolation $\Delta\in$, an extrapolation $\Delta n$, and extrapolation $\eta_{20}$ as follows.
$T_{n\text{-}i}$: 150.8° C.
$\Delta\in$: 1.49
$\Delta n$: 0.126
20η: 20.4 mPa·s Comparing Example 8 with Comparative Example 2, the extrapolation viscosity ($\eta_{20}$) of Comparative Example 2 was 20.4 mPa·s, whereas the extrapolation viscosity ($\eta_{20}$) of Example 8 was 17.7 mPa·s, and it was found lower than that of Comparative Example 2. Also, the extrapolation $\Delta n$ of Comparative Example 2 was 0.126, whereas extrapolation $\Delta n$ of Example 8 was 0.1883, a large value.

As shown above, it was found that the composition of the present application has a large value of $\Delta n$ while having a low viscosity, and furthermore, it can maintain a high miscibility with other liquid crystalline compounds.

What is claimed is:

1. A compound of general formula (1-1),

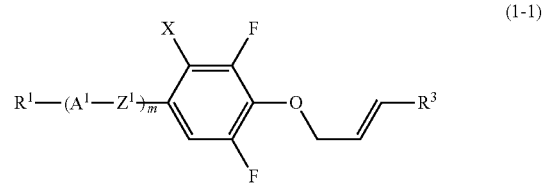

(1-1)

wherein in the formula, $R^1$ represents an alkyl group having a carbon atom number of 1 to 15 or an alkenyl group having a carbon atom number of 2 to 15, in which one group of —$CH_2$—, or two or more groups of —$CH_2$— not adjacent to each other can be replaced with a group of —O—, —S—, —COO—, —OCO— or —CO—, in which the hydrogen atom in these groups can be replaced with fluorine atom, $R^3$ represents a hydrogen atom or an alkyl group having a carbon atom number of 1 to 3, in which one group of —$CH_2$—, or two or more groups of —$CH_2$— not adjacent to each other can be replaced with a group of —O—, —S—, —COO—, —OCO— or —CO—, in which the hydrogen atom in the alkyl group can be replaced with a fluorine atom, $A^1$ is selected from the groups consisting of:

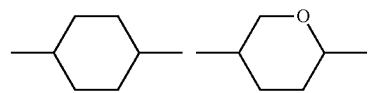

-continued

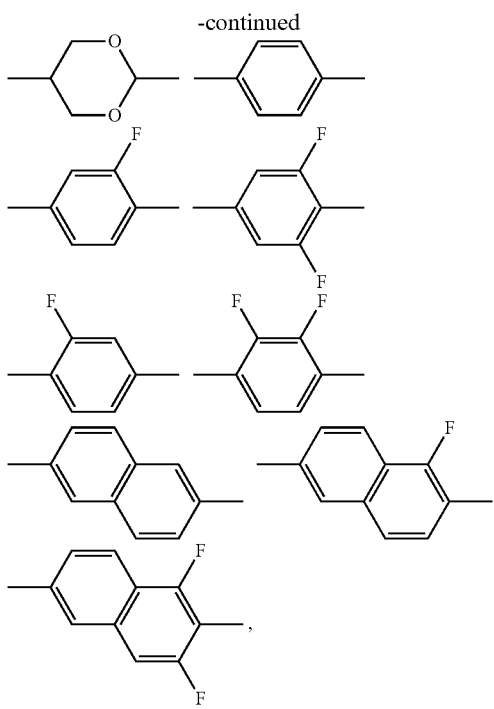

at least one of the $A^1$ groups is selected from the groups consisting of:

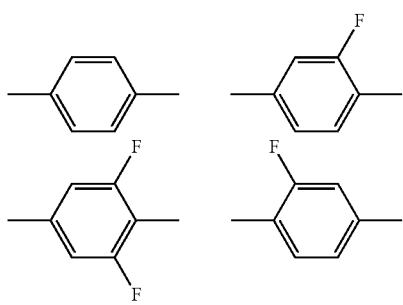

-continued

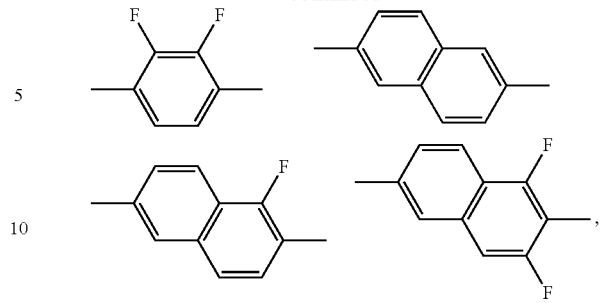

$Z^1$ represents —CH$_2$O—, —OCH$_2$—, —CF$_2$O—, —OCF$_2$—, —COO—, —OCO—, —CH$_2$CH$_2$—, —CF$_2$CF$_2$—, —CH=CH—, —CF=CF—, or a single bond;

X represents a hydrogen atom, a fluorine atom or a chlorine atom;

m represents 1 to 4, in which when m is 2 to 4, and plural $A^1$ groups exist, said plural $A^1$ group can be the same as or different from each other; and when m is 2 to 4, and plural $Z^1$ groups exist, said plural $Z^1$ groups can be the same as or different from each other.

2. The compound according to claim 1, wherein in the general formula (1), X represents the hydrogen atom or the fluorine atom.

3. The compound according to claim 1, wherein in the general formula (1), $Z^1$ represents —CH$_2$O—, —OCH$_2$—, —CH$_2$CH$_2$— or a single bond.

4. The compound according to claim 1, wherein in the general formula (1), $R^1$ represents an alkyl group having a carbon atom number of 1 to 6, or an alkenyl group having a carbon atom number of from 2 to 6.

5. A composition comprising one kind or two or more kinds of the compounds of claim 1.

6. A liquid crystal display element using the composition of claim 5.

* * * * *